US 8,268,965 B2

(12) United States Patent
Weis et al.

(10) Patent No.: US 8,268,965 B2
(45) Date of Patent: *Sep. 18, 2012

(54) TEMPLATE-DIRECTED ASSEMBLY OF RECEPTOR SIGNALING COMPLEXES

(75) Inventors: Robert M. Weis, Amherst, MA (US); Anthony L. Shrout, Northampton, MA (US); David J. Montefusco, Northampton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/653,507

(22) Filed: Dec. 14, 2009

(65) Prior Publication Data

US 2010/0121038 A1    May 13, 2010

Related U.S. Application Data

(62) Division of application No. 10/967,107, filed on Oct. 15, 2004, now Pat. No. 7,678,540.

(60) Provisional application No. 60/511,997, filed on Oct. 16, 2003.

(51) Int. Cl.
*C07K 14/00* (2006.01)
*C12N 9/00* (2006.01)

(52) U.S. Cl. .................................. 530/350; 435/183

(58) Field of Classification Search .................. None
See application file for complete search history.

(56) References Cited

U.S. PATENT DOCUMENTS

| 4,078,052 | A | 3/1978 | Papahadjopoulos et al. |
| 4,235,871 | A | 11/1980 | Papahadjopoulos et al. |
| 4,394,149 | A | 7/1983 | Szoka, Jr. et al. |
| 4,394,448 | A | 7/1983 | Szoka, Jr. et al. |
| 4,429,008 | A | 1/1984 | Martin et al. |
| 4,565,696 | A | 1/1986 | Heath et al. |
| 4,598,051 | A | 7/1986 | Papahadjopoulos et al. |
| 4,755,388 | A | 7/1988 | Heath et al. |
| 5,047,513 | A | 9/1991 | Dobeli et al. |
| 5,962,641 | A | 10/1999 | Nelson et al. |
| 6,071,533 | A | 6/2000 | Papahadjopoulos et al. |
| 6,210,707 | B1 | 4/2001 | Papahadjopoulos et al. |
| 6,214,388 | B1 | 4/2001 | Benz et al. |
| 6,426,086 | B1 | 7/2002 | Papahadjopoulos et al. |

FOREIGN PATENT DOCUMENTS

WO        2005037858        4/2005

OTHER PUBLICATIONS

Alarcon, B. Gil, D.; Delgado, P.; Schamel, W.W.A. Initiations of TCR Signaling: Regulation Within CD3 Dimers. Immunological Reviews 2003, vol. 191, pp. 38-46.
Ben-Shlomo, I; Hsu, S.Y.; Rauch, R; Kowalski, H.W.; Hsueh, A.J. Signaling Receptome: A Genomic and Evolutionary Perspective of Plasma Membrane Receptors Involved in Signal Transduction. Sci STKE, Jun. 17, 2003, 187/re9.
Brandts, J.F.; Jacobson, BS. A General Mechanism for Transmembrane Signaling Based on Clustering of Receptors. Survey and Synthesis of Pathology Research 2:107-114 (1983).
Duzgunes, N. Preparation and Quantitation of Small Unilamellar Liposomes and Large Unilamellar Reverse-Phase Evaporation Liposomes. Duzgunes, N., ed. Part A, Methods in Enzymology, vol. 367, 2003, pp. 23-27, Amsterdam: Elsevier/Academic Press.
Duzgunes, N. Fluorescence Assays for Liposome Fusion. Duzgunes, N., ed. Part D, Methods in Enzymology, vol. 372, 2003, pp. 260-274, Amsterdam: Elsevier/Academic Press.
Discher, D.E.; Eisenberg, A. Polymer Vesicles. Science, vol. 297, Aug. 9, 2002, 967-973.
Godl, K.; Wissing, J.; Kurtenbach, A.; Habenberger, P.; Blencke, S.; Gutbrod, H.; Salassidis, K.; Stein-Gerlach, M.; Missio, A.; Cotten, M.; Daub, H. An Efficient Proteomics Method to Identify the Cellular Targets of Protein Kinase Inhibitors. PNAS, Dec. 23, 2003, vol. 100, No. 26, 15434-39.
Heldin, C-H. Dimerization of Cell Surface Receptors in Signal Transduction. Cell. vol. 80, Jan. 27, 1995, 213-223.
Mann, M.; Jensen, O.N. Proteomic Analysis of Post-translational Modifications. Nature Biotechnology, vol. 21, Mar. 2003, 255-261.
Martin, M.U.; Wesche, H. Summary and Comparison of the Signaling Mechanisms of the Toll/Interleukin-1 Receptor Family. Biochimica et Biophysica Acta 1592, 2002, 265-280.
Mui, B.; Chow, L.; Hope, M.J. Extrusion Technique to Generate Liposomes of Defined Size. Part A, Methods in Enzymology, vol. 367, 2003, pp. 3-14, Duzgunes, N., ed. Amsterdam: Elsevier/Academic Press. Niu, X-L.; Peters, K.G.; Kontos, C.D. Deletion of the Carboxyl Terminus of Tie2 Enhances Kinase Activity, Signaling and Function. Journal of Biological Chemistry. vol. 277, No. 35, Issue of Aug. 30, 2002, 31768-773.
Pawson, T.; Nash, P. Assembly of Cell Regulatory Systems Through Protein Interaction Domains. Science, vol. 300, Apr. 18, 2003, 445-452.
Penuel, E.; Schaefer, G.; Akita, R.W.; Sliwkowski, M.X. Structural Requirements for ErbB2 Transactivation. Seminars in Oncology, vol. 28, No. 6, Dec. 18, 2001, pp. 36-42.

(Continued)

*Primary Examiner* — Ruixiang Li
(74) *Attorney, Agent, or Firm* — Reinhart Boerner Van Deuren s.c.

(57) ABSTRACT

Transmembrane receptors in the signaling pathways of bacterial chemotaxis systems influence cell motility by forming noncovalent complexes with the cytoplasmic signaling proteins to regulate their activity. The requirements for receptor-mediated activation of CheA, the principal kinase of the *Escherichia coli* chemotaxis signaling pathway, can be demonstrated using self-assembled clusters of a receptor fragment (CF) derived from the cytoplasmic domain of the aspartate receptor, Tar. Histidine-tagged Tar CF can be assembled on the surface of unilamellar vesicles via a lipid containing the Nickel-nitrilotriacetic acid moiety as a headgroup. The stability of such a complex can be controlled by the properties of the template including the size and composition, which can be used, for example, to vary the 2-dimensional concentration of receptor fragments. Surface-assembled CF is also found to serve as a substrate for receptor methylation, which is catalyzed by the receptor transferase. Since neither CheA activation nor CF methylation is observed in comparable samples in the absence of vesicles, it is concluded that surface-templating generates the organization among CF subunits required for biochemical activity.

25 Claims, 8 Drawing Sheets

OTHER PUBLICATIONS

Robertson, S.C.; Tynan, J.A.; Donoghue, D.J. RTK Mutations and Human Syndromes—When Good Receptors Turn Bad. Trends in Genetics, Jun. 2000, vol. 16, No. 6, pp. 265-271.

Singer, S.J.; Nicolson, G.L. The Fluid Mosaic Model of the Structure of Cell Membranes. Science, vol. 175, Feb. 18, 1972, 720-731.

Stroud, R.M.; Wells, J.A. Mechanistic Diversity of Cytokine Receptor Signaling Across Cell Membranes. Sciences STKE 2004/231, re7.

Changeux JP; Thiery J; Tung, Y; Kittel C. On the Cooperativity of Biological Membranes. Proc. Natl. Acad. Sci. USA, 1967, 57, 335-341.

Changeux JP; Edelstein SJ. Allosteric Mechanisms of Signal Transduction. Science, 2005, 308, 1424-1428.

Grasberger, B; Minton AP; Delisi C; Metzger H. Interaction of between proteins localized in membranes. Proc. Natl. Acad. Sci. USA, 1986, 83, 6258-6262.

Kornberg RD; McConnell HM. Lateral diffusion of phospholipids in a vesicle membrane. Proc. Natl. Acad. Sci. USA. 1971. 68, 2564-2568.

Koshland, DE, Jr; Némethy G; Filmer D. Comparison of experimental binding data and theoretical models in proteins containing subunits. Biochemistry, 1966, 5, 365-385.

Lim WA. The modular logic of signaling proteins: building allosteric switches from simple binding domains. Cur. Opin. Stuct. Biol. 2002, 12, 61-68.

Monod J; Wyman J; Changeux JP. On the nature of allosteric transitions: a plausible model. J. Mol. Biol. 1965, 12, 88-118.

Uzgiris, EE; Kornberg RD. Two-dimensional crystallization technique for imaging macromolecules, with application to antigen-antibody-complement complexes. Nature, vol. 301, Jan. 13, 1983, pp. 125-129.

Thess, A; Hutschenreiter, S; Hofmann, M; TampéR; Baumeister W; Guckenberger R. Specific Orientation and Two-dimensional Crystallization of the Proteasome at Metal-chelating Lipid Interfaces. The Journal of Biological Chemistry. vol. 277, No. 39, Issue of Sep. 27, 2002, pp. 36321-36328.

Smith LM; Parce JW; Smith BA; McConnell HM. Antibodies bound to lipid haptens in model membranes diffuse as rapidly as the lipids themselves. Proc. Natl. Acad. Sci. USA, vol. 76, No. 9, pp. 4177-4179, Sep. 1979.

Shimizu, TS; Le Novére, N; Levin MD; Beavil AJ; Sutton BJ; Bray D. Molecular model of a lattice of signalling proteins involved in bacterial chemotaxis. Nature Cell Biology, vol. 2 Nov. 2000, pp. 792-796.

Frey, W; Schief WR JR; Pack DW; Chen C-T; Chilkoti A; Stayton P; Vogel V; Arnold FH. Two-dimensional protein crystallization via metal-ion coordination by naturally occurring surface histidines. Proc. Natl. Acad. Sci USA, vol. 93, pp. 4937-4941, May 1996.

Celia H; Wilson-Kubalek E; Millgan RA; Teyton L. Structure and function of a membrane-bound murine MHC class I molecule. Proc. Natl. Acad. Sci USA, vol. 96, pp. 5634-5639, May 1999.

Changeux, J-P; Edelstein SJ. Allosteric mechanisms in normal and pathological nicotinic acetylcholine receptors. Current Opinion in Neurobiology 2001, 11:369-377.

Changeux, J-P; Edelstein SJ. Allosteric Receptors after 30 Years. Neuron, vol. 21, 959-980, Nov. 1998.

Francis NR; Levit MN; Shaikh TR; Melanson LA; Stock JB; Derosier DJ. Subunit Organization in a Soluble Complex of Tar, CheW and CheA by Electron Microscopy. The Journal of Biological Chemistry, Sep. 27, 2002, vol. 277, No. 39, pp. 36755-36759.

Liu Y; Levit M; Lurz R; Surrette MG; Stock JB. Receptor-Mediated Protein Kinase Activation in Receptor Signaling Complexes. Biochemistry, 1999, vol. 38, pp. 6651-6658.

Shrout Al; Montefusco DJ; Weis RM. Template-Directed Assembly of Receptor Signaling Complexes. Biochemistry, 2003, vol. 42, pp. 13379-13385.

Ninfa EG; Stock A; Mowbray S; Stock J. Reconstitution of the Bacterial Chemotaxis Signal Transduction System from Purified Components. The Journal of Biological Chemistry, May 25, 1991, vol. 266, No. 15, pp. 9764-9770.

Shrout AL; Montefusco DJ; Weis RM. Activation of Cellular Signaling Pathways by Template-Directed Assembly of Receptor Fragments, Abstract; Annual Meeting of the American Society for Biochemistry and Molecular Biology, Apr. 13-17, 2003, San Diego, California.

Asinas AE; Weis RM. Protein Interactions and Signaling in a Self-Assembled Receptor System, Abstracts; Divisions of Biological Chemistry, 226th National Meeting of the American Chemical Society, Sep. 7-11, 2003, ACS (2003), p. 8613.

Li G; Weis RM. Covalent Modification Regulates Ligand Binding to Receptor Complexes in the Chemosensory System of *Escherichia coli*. Cell, Feb. 4, 2000, vol. 100, Cell Press, pp. 357-365.

Dietrich C; Boscheinen O; Scharf KD; Schmitt L; Tampe R. Functional Immobilization of a DNA-Binding Protein at a Membrane Interface via Hisidine Tag and Synthetic Chelator Lipids. Biochemistry, 1996, vol. 35, No. 4, pp. 1100-1105.

Farsad K; Ringstad N; Takei K; Floyd SR; Rose K; De Camilli P. Generation of High Curvature Membranes Mediated by Direct Endophilin Bilayer Interactions. The Journal of Cell Biology, Oct. 15, 2001, vol. 155, No. 2, pp. 193-200, The Rockefeller University Press.

Yamamoto S; Kubotsu K; Kida M; Dondo K; Matsuura S; Uchiyama S; Yonekawa O; Kanno T. Automated Homogenous Liposome-Based Assay System for Total Complement Activity. Clinical Chemistry, 1995, vol. 41, No. 4, pp. 586-590.

Wu J; Li J; Li G; Long DG; Weis RM. The Receptor Binding Site for the Methyltransferase of Bacterial Chemotaxis Is Distinct from the Sites of Methylation. Biochemistry, 1996, vol. 35, No. 15, pp. 4984-4993.

Kubalek EW; Le Grice SFJ; Brown PO. Two-Dimensional Crystallization of Histidine-Tagged, HIV-1 reverse Transcriptase Promoted by a Novel Nickel-Chelating Lipid. Journal of Structural Biology, 1994, vol. 113, pp. 117-123.

Farrens et al., Requirement for Rigid-body motion of transmembrane helices for light activation of Rhodopsin. Science 274:768-770, 1996.

Tuthill, Tobias J. et al: "Characterization of Early Steps in the Poliovirus Infection Process: Receptor-Decorated Liposomes Induce Conversion of the Virus to Membrane-Anchored Entry-Intermediate Particles." J. of Virology, vol. 80, No. 1, Jan. 2006, pp. 172-180.

Zhang, Xuewu et al: "An Allosteric Mechanism for Activation of the Kinase Domain of Epidermal Growth Factor Receptor." Cell, vol. 125, No. 6, Jun. 16, 2006, pp. 1137-1149.

Waters, E.K. et al: "Restoring Full Biological Activity to the Isolated Ectodomain of an Integral Membrane Protein." Biochemistry, Am. Chemical Society, Easton, PA.; US, vol. 45, No. 11, Feb. 25, 2006, pp. 3769-3774.

Dietrich, C.; Schmitt, L.; and Tampe, R.; Molecular Organization of Histidine-tagged Biomolecules at Self-assembled Lipid Interfaces Using a Novel Class of Chelator Lipids; Proc. Natl. Acad. Sci. USA, Sep. 1995, 9014-9048, vol. 92.

Levit, MN., Lui, Y., Stock, JB.; Mechanism of CheA protein kinase activation in receptor signaling complexes. Biochmestry. vol. 38, 1999, pp. 6651-6658.

Schmitt, L., Dietrich, C., Tampe R. Synthesis and Characterization of Chelator-Lipids for Reversible Immobilization of Engineered Proteins at Self-Assembled Lipid Interfaces; J. Am, Chem. Soc., 1994, 8485-8491, vol. 116, No. 19.

TEMPLATE-DIRECTED ASSEMBLY OF RECEPTOR SIGNALING COMPLEXES

This application is a divisional of U.S. application Ser. No. 10/967,107 filed Oct. 15, 2004, now U.S. Pat. No. 7,678,540 which claims priority benefit of provisional application Ser. No. 60/511,997 filed Oct. 16, 2003, which is incorporated herein by reference in its entirety.

The United States government has certain rights to this invention pursuant to Grant No. R01 GM532120 from the National Institutes of Health to the University of Massachusetts.

BACKGROUND OF THE INVENTION

The organization and asymmetry inherent in cell membranes creates an environment in which receptor proteins can effectively convey information between the inside and outside of the cell (1). The reduction in the degrees of freedom experienced by transmembrane and peripheral membrane proteins provides a strong driving force for lateral organization, which can be essential for function, e.g. ligand-induced clustering (2). These factors are in effect at the plasma membrane inner leaflet, where the assembly and regulation of signaling components often occur (3-5). In the chemotaxis signal transduction pathway of *Escherichia coli*, complexes of transmembrane receptors and cytoplasmic signaling proteins (6,7) regulate protein phosphorylation through ligand-receptor interactions and receptor covalent modification (8-12). This transduction pathway is coupled to cell motility, which biases the swimming behavior of the cell in attractant and repellant gradients (13).

Several lines of evidence suggest that receptors are clustered in the cell membrane (14-16) and that close associations between receptors of different ligand specificity are important in signaling (17-21). The aspartate receptor (Tar) is representative of a large class of receptors in the bacterial chemotaxis pathways (23,24), which are also known as the methyl-accepting chemotaxis proteins (MCPs) due to the enzyme-catalyzed receptor methylation and demethylation reactions that are essential for sensory adaptation (25). The structure of the Tar dimer (FIG. 1A) provides insights into the basis for the possible requirement of receptor clusters in signaling. *Escherichia coli* has four MCPs (Tar, Tsr, Tap, Trg) and an aerotaxis receptor (Aer) that are distinguished by ligand binding specificities, which reside primarily in the n-terminal extra-cytoplasmic domain. The dimeric organization of MCPs is evident in crystal structures of the aspartate receptor (Tar) ligand binding domain (26,27) and the serine receptor (Tsr) cytoplasmic domain (28). The significantly greater homology among the c-terminal domains of these five receptors provides the basis for common interactions among a set of cytoplasmic signaling proteins (23), which generate the excitatory and adaptive responses to the chemotactic stimuli (reviewed in reference 29). In addition, the Tsr cytoplasmic domain is organized as a trimer-of-dimers in the crystal structure (28). The subunit interactions that lead to the trimer-of-dimer structure are apparently important for the intact receptor in the cell, since mutations in conserved amino acid residues at the trimer-of-dimer contact site disrupt chemotaxis and receptor clustering (21). Thus, within the context of these heterogeneous receptor clusters, the overall signaling protein (e.g., CheA in *E. coli*) activity reflects the influences of the various independent inputs, detected by the MCPs and Aer.

Biochemical investigations using membrane preparations of either Tar or Tsr with the purified signaling proteins have clarified some of the properties of CheA activation and regulation (8-12). Notable observations include the substantial increase in CheA activity (>100-fold) that accompanies signaling complex formation, the stimulating influence of receptor methylation on CheA activity, and the inhibitory influence of ligand binding. However, membrane samples of the MCPs that are used in such biochemical experiments are frequently isolated from cells expressing the receptor at elevated levels, which can result in complex and heterogeneous samples (30). Also, receptor reconstitution is labor-intensive, and the conditions that maintain a high level of activity while also preserving the vectoral and lateral organization required for function can be difficult to find (31,32). For example receptor organization leads to purification difficulties involving procedures that invariably require two-phase detergent containing systems. Low yields are typical and represent an impediment to widespread use of such receptors in cell-free assay systems. An added disadvantage to the use of a homogeneous assay is the detergent, itself, which disrupts the interactions between receptor proteins on a membrane.

To circumvent the difficulties that typically plague the use of such samples, studies of CheA activation have used soluble cytoplasmic receptor fragments (CFs). In many instances CFs are unable to activate CheA, but those that do seem to via oligomerization, which occurs synergistically with CheW and CheA binding (33-36). While this approach has helped to elucidate the enzymatic properties of signaling complexes, the formation of these complexes is limited to certain relative concentrations of CF, CheW and CheA, and is undesirably sensitive to variations in the tendency of different CFs to oligomerize. As a result, a comprehensive study of the factors important for CheA activation remains a continuing research goal.

The foregoing background information, together with various aspects of the prior art are disclosed more fully by the following publications, as referenced herein.

1. Singer, S. J., and Nicholson, G. L. (1972) *Science* 175, 720-731.
2. Brandts, J. F., and Jacobson, B. S. (1983) *Surv. Syn. Pathol. Res.* 2, 107-114.
3. Pawson, T., and Nash, P. (2003) *Science* 300, 445-452.
4. Jordan, M. S., Singer, A. L. and Koretzky, G. A. (2003) *Nat. Immmunol.* 4, 110 116.
5. Sheng, M., and Sala, C. (2001) *Annu. Rev. Neurosci.* 24, 1-29.
6. Gegner, J. A., Graham, D. R., Roth, A. F., and Dahlquist, F. W. (1992) *Cell* 70, 975-982.
7. Schuster, S. C., Swanson, R. V., Alex, L. A., Bourret, R. B., and Simon, M. I. (1993) *Nature* 365, 343-347.
8. Borkovich, K. A., Alex, L. A., and Simon, M. I. (1992) *Proc. Natl. Acad. Sci. USA* 89, 6756-6760.
9. Li, G., and Weis, R. M. (2000) *Cell* 100, 357-365.
10. Bornhorst, J. A., and Falke, J. J. (2000) *Biochemistry* 39, 9486-9493.
11. Levit, M. N., and Stock, J. B. (2002) *J. Biol. Chem.* 277, 36760-36765.
12. Bornhorst, J. A., and Falke, J. J. (2003) *J. Mol. Biol.* 326, 1597-1614.
13. Adler, J. (1975) *Annu. Rev. Biochem.* 44, 341-356.
14. Maddock, J. R. and L. Shapiro, L. (1993) *Science* 259, 1717-1723.
15. Sourjik, V., and Berg, H. C. (2000) *Mol. Microbiol.* 37, 740-751.
16. Cantwell, B. J., Draheim, R. R., Weart, R. B., Nguyen, C., Stewart, R. C., and Manson, M. D. (2003) *J. Bacteriol.* 185, 2354-2361.

17. Wu, J., Li, J., Li, G., Long, D. G., and Weis, R. M. (1996) *Biochemistry* 35, 4984-4993.
18. Li, J., Li, G., and Weis, R. M. (1997) *Biochemistry* 36, 11851-11857.
19. Le Moual, H., Quang, T., and Koshland, D. E., Jr. (1997) *Biochemistry* 36, 13441-13448.
20. Gestwicki, J. E., and Kiessling, L. L. (2002) *Nature* 415, 81-84.
21. Ames, P., Studdert, C. A., Reiser, R. H., and Parkinson, J. S. (2002) *Proc. Natl. Acad. Sci. USA* 99, 7060-7065.
23. H. Le Moual, H., and Koshland, D. E., Jr. (1996) *J. Mol. Biol.* 261, 568-585.
24. Zhulin, I. B. (2001) *Adv. Microb. Physiol.* 45, 157-198.
25. Springer, M. S., Goy, M. F., and Adler, J. (1979) *Nature* 280, 279-284.
26. Milburn, M. V., Privé, G. G., Milligan, D. L., Scott, W. G., Yeh, J., Jancarik, J., Koshland, D. E. Jr., and Kim, S.-H. (1991) *Science* 254, 1342-1347.
27. Yeh, J. I., Biemann, H. P., Prive, G. G., Pandit, J., Koshland, D. E., Jr., and Kim, S.-H. (1996) *J. Mol. Biol.* 262, 186-201.
28. Kim, K. K., Yokota, H., and Kim S.-H. (1999) *Nature* 400, 787-792.
29. Falke, J. J., Bass, R. B., Butler, S. L., Chervitz, S. A., and Danielson, M. A. (1997) *Annu. Rev. Cell Dev. Biol.* 13, 457-512.
30. Weis, R. M., Hirai, T., Chalah, A., Kessel, M., Peters, P. J., and Subramaniam, S. (2003) *J. Bacteriol.* 185, 3636-3643.
31. Ninfa, E. G., Stock, A., Mowbray, S., and Stock J. (1991) *J. Biol. Chem.* 266, 9764-9770.
32. Bogonez, E., and Koshland, D. E., Jr. (1985) *Proc. Natl. Acad. Sci. USA* 82, 4891-4895.
33. Ames, P., and Parkinson, J. S. (1994) *J. Bacteriol.* 176, 6340-6348.
34. Cochran, A. G., and Kim, P. S. (1996) *Science* 271, 1113-1116.
35. Liu, Y., Levit, M., Lurz, R., Surette, M. G., and Stock, J. B. (1997) *EMBO J.* 16, 7231-7240.
36. Francis, N. R., Levit, M. N., Shaikh, T. R., Melanson, L. A., Stock, J. B., and DeRosier, D. J. (2002) *J. Biol. Chem.* 277, 36755-36759.
37. Schmitt, L., Dietrich, L., and Tampé, R. J. (1994) *J. Am. Chem. Soc.* 166, 8485-8491.
38. Kott, L., Braswell, E. M., Shrout, A. L., and Weis, R. M. (2004) *Biochim. Biophys. Acta.* 1696, 131-140.
39. Surette, M. G., Levit, M., Liu, Y., Lukat, G., Ninfa, E. G., Ninfa, A., and Stock, J. B. (1996) *J. Biol. Chem.* 271, 939-945.
40. Norby, J. G. (1988) *Methods Enzymol.* 156, 116-119.
41. Nagle, J. F., and Tristram-Nagle, S. (2000) *Biochim. Biophys. Acta* 1469, 159-195.
42. Luecke, H., Schobert, B., Richter, H. T., Cartailler, J. P., and Lanyi, J. K. (1999) *J. Mol. Biol.* 291, 899-911.
43. Ren, G., Reddy, V. S., Cheng, A., Melnyk, P., and Mitra, A. K. (2001) *Proc. Natl. Acad. Sci. USA* 98, 1398-1403.
44. Heymann, J. A. W., Sarker, R., Hirai, T., Shi, D., Milne, J. L. S., Maloney, P. C., and Subramaniam, S. (2000) *EMBO J.* 20, 4408-4413.
45. Dunten, P., and Koshland, Jr., D. E. (1991) *J. Biol. Chem.* 266, 1491-1496.
46. Levit, M. N., Liu, Y., and Stock, J. B. (1999) *Biochemistry* 38, 6651-6658.
47. Boukhvalova, M., VanBruggen, R., and Stewart, R. C. (2002) *J. Biol. Chem.* 277, 23596-23603.
48. Mutoh, N., Oosawa, K., and Simon, M. I. (1986) *J. Bacteriol.* 167, 992-998.
49. Borkovich, K. A., and Simon, M. I. (1990) *Cell.* 63, 1339-1348.
50. Kehry, M. R., and Dahlquist, F. W. (1982) *J. Biol. Chem.* 257, 10378-10386.
51. Terwilliger, T. C., and Koshland, D. E. Jr. (1984) *J. Biol. Chem.* 259, 7719-7725.
52. Kehry, M. R., Engstrom, P., Dahlquist, F. W., and Hazelbauer, G. L. (1983) *J. Biol. Chem.* 258, 5050-5055.
53. Crowe, J., Dobeli, H., Gentz, R., Hochuli, E., Stuber, D., and Henco, K. (1994) *Methods Mol. Biol.* 31, 371-387.
54. Jones, C., Patel, A., Griffin, S., Martin, J., Young, P., O'Donnell, K., Silverman, C., Porter, T., and Chaiken, I. (1995) *J. Chromatogr. A* 707, 3-22.
55. Terpe, K. (2003) *Appl. Microbiol. Biotechnol.* 60, 523-533.
56. Nieba, L., Nieba-Axmann, S. E., Persson, A., Hamalainen, M., Edebratt, F., Hansson, A., Lidholm, J., Magnusson, K., Karlsson, A. F., and Pluckthun, A. (1997) *Anal. Biochem.* 252, 217-228.
57. Gershon, P. D., Khilko, S. (1995) *J. Immunol. Methods* 183, 65-76.
58. Frey, W., Schief, W. R. Jr., Pack, D. W., Chen, C. T., Chilkoti, A., Stayton, P., Vogel, V., and Arnold, F. H. (1996) *Proc. Natl. Acad. Sci. USA* 93, 4937-4941.
59. Celia, H., Wilson-Kubalek, E., Milligan, R. A., Teyton, L. (1999) *Proc. Natl. Acad. Sci. USA* 96, 5634-5639.
60. Thess, A., Hutschenreiter, S., Hofmann, M., Tampé, R., Baumeister, W., and Guckenberger, R. (2002) *J. Biol. Chem.* 277, 36321-36328.

BRIEF DESCRIPTION OF THE DRAWINGS

With reference to the figures and accompanying discussion and examples, abbreviations used herein include: MCP, methyl-accepting chemotaxis protein; Tar, aspartate receptor; Tsr, serine receptor; Tap, dipeptide receptor; Trg, ribose/galactose receptor; Aer, aerotaxis receptor; CF, cytoplasmic fragment; DOPC, 1,2-dioleoyl-sn-glycero-3-phosphocholine; DOGS-NTA, 1,2-dioleoyl-sn-glycero-3-{[N(-amino-1-carboxypentyl)iminodiacetic acid]-succinyl}ammonium salt); DOGS-NTA-Ni$^{2+}$'DOGS-NTA Nickel Salt; SUV, small unilamellar vesicle; LUV, large unilamellar vesicle; Ni—NTA, nickel-nitrilotriacetic acid; tod, trimer-of-dimer; SAM, s-adenosyl-L-methionine; SAH, s-adenosyl-L-homocysteine; meth-CF, carboxyl-methylated CF; CheR, methyltransferase; NAD$^+$, nicotinamide-adenine dinucleotide (oxidized form); NADH, nicotinamide adenine dinucleotide (reduced form); ATP, adenosine triphosphate; ADP, adenosine diphosphate; GTP, guanine triphosphate; Y, CheY; PK, pyruvate kinase; LDH, lactate dehydrogenase.

Figure 1:
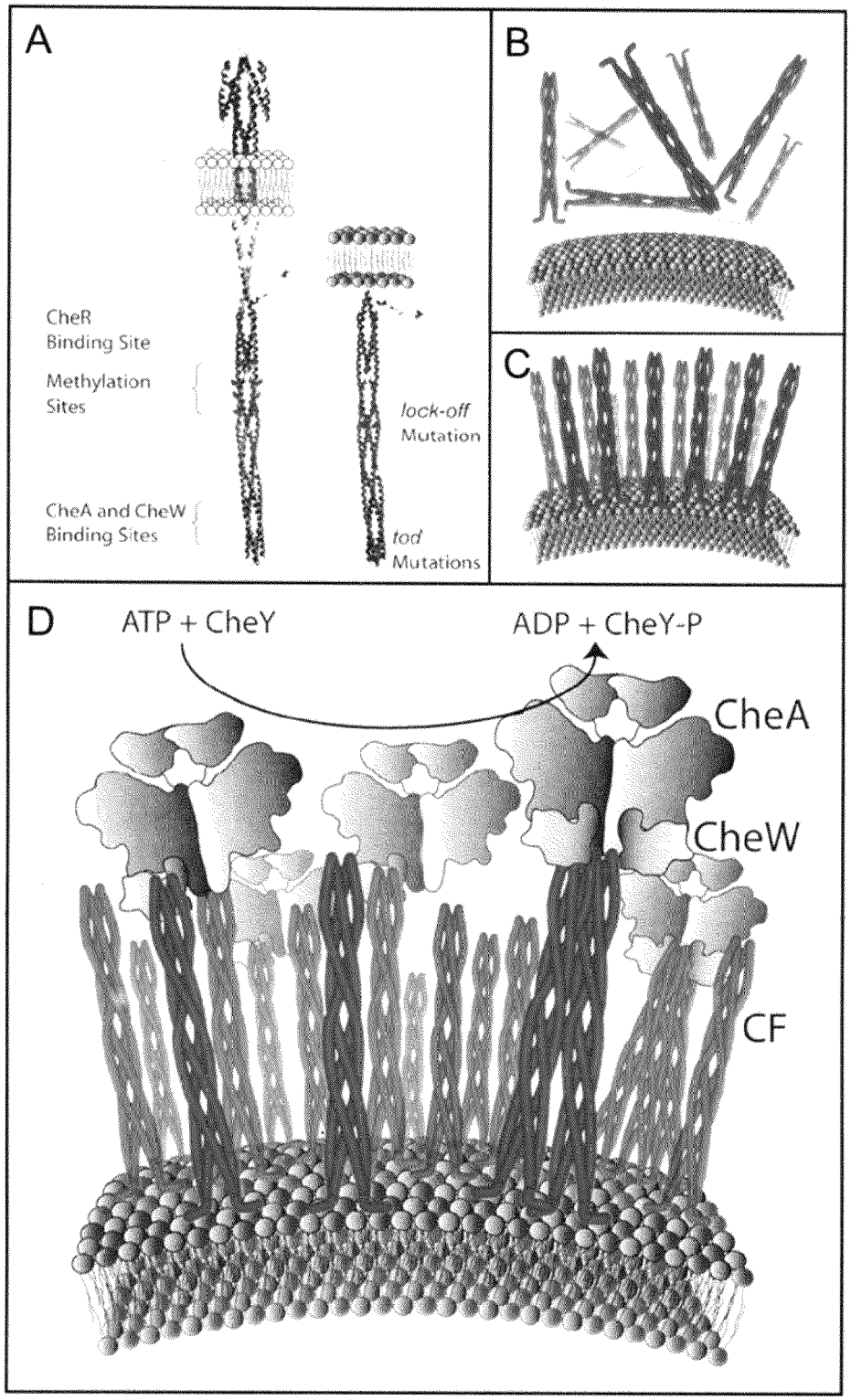
FIG. 1. Receptor Structure and Surface-Templated Complex Assembly. A: A non-limiting model of the chemotaxis receptor dimer at left is based primarily on recognized ligand binding and cytoplasmic domain crystal structures. One subunit is rendered gray, the other to indicate functional regions: ligand-binding domain, transmembrane segments, linker region and the cytoplasmic domain. The methylation sites (Q295, E302, Q309, E491) are depicted with space-filling representations. The membrane-anchored CF dimer at right indicates positions of the S461L lock-off mutation and two tod mutations (E383A, V382P) in space-filling representation. B to D: Illustrations depicting CF binding to the SUV surface. CFs are shown as dimers for simplicity.
Figure 2:
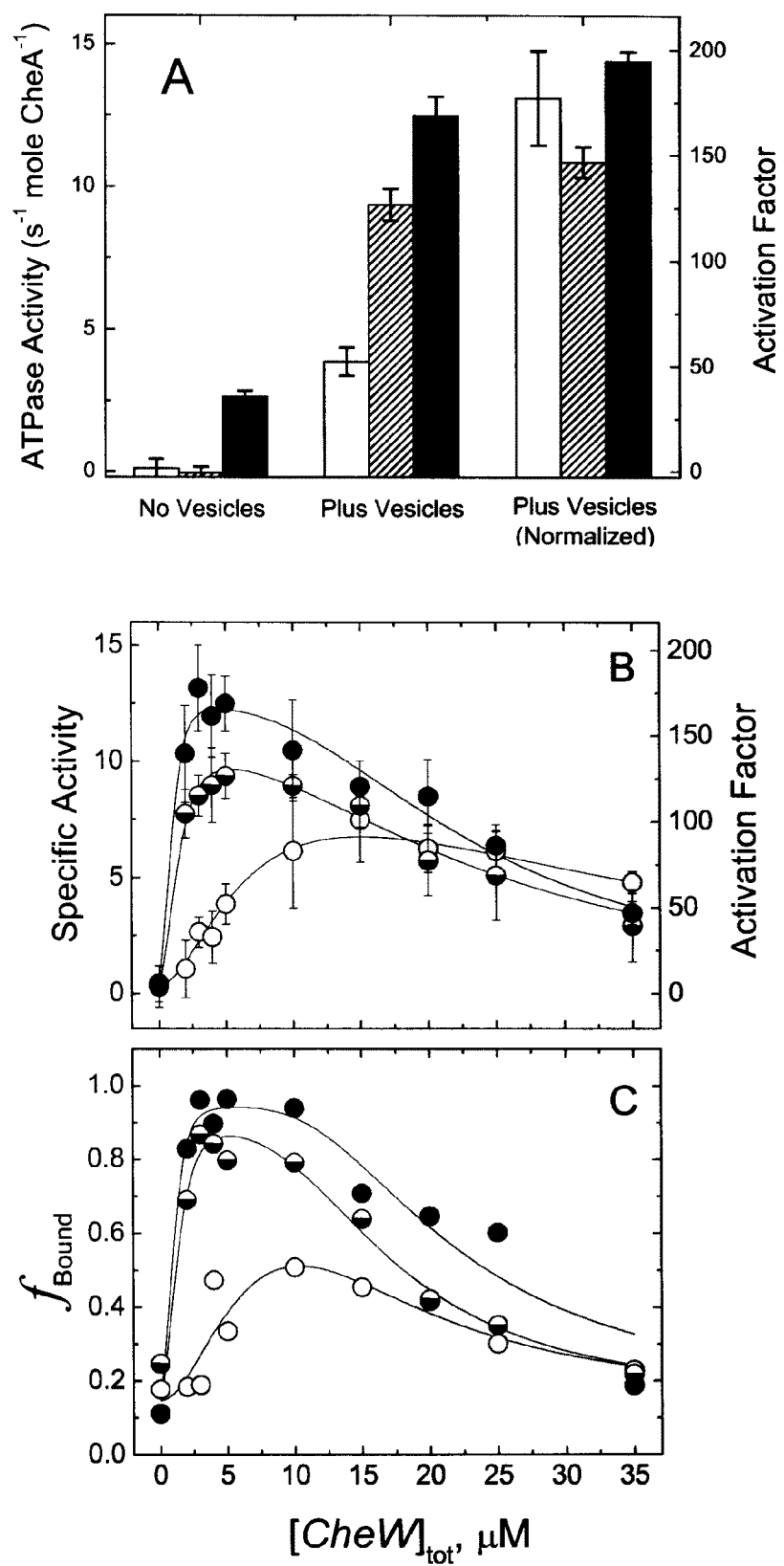
FIG. 2. CheA Activation on Vesicles Surfaces. A: Left and right-hand scales are CheA activity (s$^{-1}$) and the fold-increase of CheA activity in complexes relative to CheA dimers in solution, respectively. Activities (±standard error of three samples) were measured on samples (1.2 μM CheA, 5 μM CheW and 30 μM CF) containing CF in low (EEEE), intermediate (QEQE) and high (QQQQ) modification levels (open, striped and filled bars, respectively) in the absence of SUVs ('No Vesicles', left) and with SUVs ('Plus Vesicles', middle). The 'Plus Vesicles (Normalized)' data, on the right, are normalized by the fraction of bound CheA, which was determined in parallel by sedimentation. The normalized activities are averages of six samples (±standard error) determined at different CheW concentrations (3, 4, 5, 10, 15, 20 μM). B: CheA activities of complexes, prepared as described below, with CF in different modification states (EEEE, ○; QEQE, ◒; QQQQ, ●). Each point is an average of three samples (±standard deviation). Curves are fits to the data conducted as described below. C: The CheW-dependence of CheA binding. Fits of these data generated estimates for $K_{complex}$ in $CF_{QQQQ}$, $CF_{QEQE}$ and $CF_{EEEE}$-containing complexes, as described below.
Figure 3:
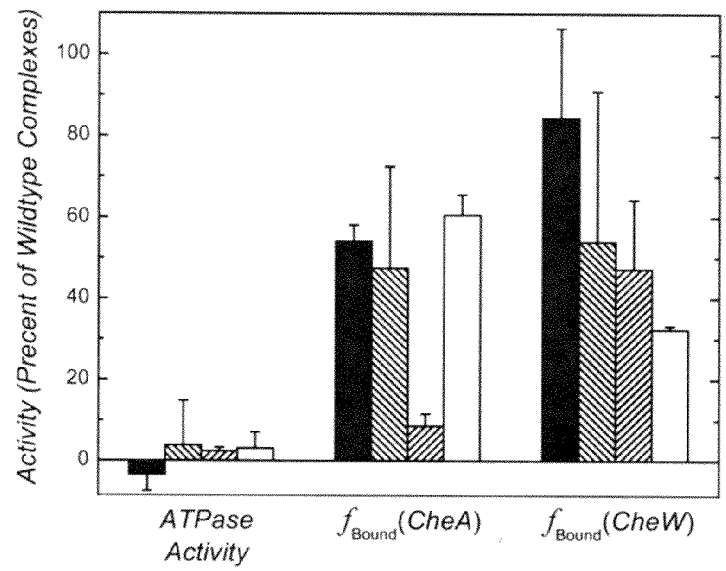
FIG. 3. Effects of CF Mutations on Activity and Binding. The activities and $f_{Bound}$ values are expressed as percentages relative to the complexes containing wildtype CF under the same conditions (Table 1) for the lock-off mutant CF:S461L (in the QEQE level of covalent modification, black bars) and the tod mutants CF:E383A and CF:V382P (the EEEE and QQQQ forms of CF:E383A are represented by left and right-slanting striped bars, respectively; the QEQE form of CF:V382P is represented by open bars). Uncertainties are error-propagated values using standard errors of the mean determined on triplicate samples with the wildtype and mutant complexes.

Samples contained 250 μM DOPC, 300 μM DOGS-NTA-Ni$^{2+}$ as SUVs, 1.2 μM CheA, 30 μM total CF, and either 4 μM or 15 μM CheW (in the QQQQ-CF and EEEE-CF containing samples, respectively).

SUMMARY OF THE INVENTION

In light of the foregoing, it is an object of the present invention to provide cytoplasmic receptor fragments or components, complexes therewith and/or method(s) for their assembly, thereby overcoming various deficiencies and shortcomings of the prior art, including those outlined above. Accordingly, it is another object of the present invention to provide a biomimetic approach to signaling complex formation without receptor reconstitution and unlimited by relative concentrations of receptor fragment/component, signaling protein, or adaptor protein.

It is another object of the present invention to provide a method for receptor organization and/or signaling complex formation avoiding purification difficulties that are typical of membrane proteins, and without regard to fragment oligomerization. In a related manner, it is also an object of this invention to provide a method for assembly of receptor fragments conducive to receptor interaction and enhanced signaling activity, such a method as can be used in conjunction with analysis of a cell signal transduction pathway and/or cell-free assay of a biochemical reaction associated therewith.

Other objects, features, benefits and advantages of the present invention will be apparent from this summary and its descriptions of certain embodiments, and will be readily apparent to those skilled in the art having knowledge of receptor fragment assembly, cell signal transduction pathways and assay techniques derived therefrom. Such objects, features, benefits and advantages will be apparent from the above as taken into conjunction with the accompanying examples, data, figures and all reasonable inferences to be drawn therefrom.

The present invention relates to receptor signaling complexes and the assembly of such complexes over a wide range of adaptor and/or signaling protein identities and concentrations. For purposes of illustration, small unilamellar vesicles (SUVs) prepared by sonication that contain a nickel-chelating lipid were used to template the assembly of histidine-tagged CF derived from E. coli Tar onto the outer leaflet of the SUV membrane bilayer. The organization of CF produced by vesicle binding was found to resemble the environment of the cell membrane inner leaflet sufficiently well to promote the assembly of active signaling complexes and to restore enzyme-catalyzed methylation of the CF. The vesicle (or solid support) templating approach described herein can be applied generally where the function of signaling proteins can be enhanced by the organizing influence of a simulated or biomimetic cell membrane environment.

Accordingly, the present invention comprises a biomimetic signaling complex comprising 1) a plurality of cytoplasmic proteinaceous receptor fragment or component having at least one amino acid residue with affinity for a selective membrane/template binding or chelating interaction; and 2) a signaling protein. Optionally, such a complex can include an adaptor protein of the sort that may be used to facilitate complexation of the signaling protein with the receptor fragment component. A receptor fragment may provide enzyme (catalytic) activity or function as a substrate; fragment templating may be utilized, as needed, to restore such activity or function. Generally, such a fragment component corresponds to the cytoplasmic or intracellular domain of a transmembrane receptor molecule—in certain embodiments, one or more methyl-accepting chemotaxis proteins—as can be chemically or structurally modified to enhance complexation, and one or more amino acid residues associated therewith capable of selective membrane/template chelation with a metal-containing moiety thereof. The aforementioned signaling protein is, typically, an enzyme active in or having a role in a particular cellular signal transduction pathway. Where conducive to biochemical activity, such a complex can comprise a mixture of receptor fragments and/or other membrane-associated components, including other naturally occurring lipids and adaptor proteins. In certain embodiments, the signaling protein can be a kinase of the E. coli chemotaxis signaling pathway. Corresponding thereto, the receptor fragment component can be one or more of several known cytoplasmic fragments of the methyl-accepting chemotaxis proteins of E. coli, modified with one or more histidine residues. In certain embodiments of this invention, such a component can be a polyhistidine-modified aspartate receptor fragment.

As described above, one embodiment or implementation of this invention is demonstrated with a genetically-encoded histidine tag fused to the cytoplasmic-domain of Tar-CF. Templating is promoted through a specific noncovalent interaction with the modified phospholipid DOGS-NTA-Ni$^{2+}$. The histidine tag fusion shows that other genetically engineered polypeptide segments known in the art can be used to anchor the receptor fragment and/or signaling protein to the template. Such fusion proteins may involve naturally-occurring proteinacious binding domains, which are known to bind to certain lipid molecules, that by analogy to DOGS-NTA-Ni$^{2+}$ can be incorporated into the template; or short peptides of known sequence, which can be incorporated into the template in a similar manner. The genetically engineered segment may also be used to introduce at least one amino acid that either permits the covalent attachment of the receptor fragment to the template, or the covalent attachment of a moiety that engenders specific attachment to the template. An example of the former includes the introduction of a cysteine (Cys) residue, which is known to exhibit specific reactivity toward maleimide, and reacts to form a covalent adduct. The maleimide moiety can be made available as the head group in a synthetic lipid molecule, by analogy to DOGS-NTA, and thereby facilitate direct covalent attachment of the receptor (via cysteine) to the template. An example of a second mode of attachment is illustrated by the introduction of a known biotinylation recognition sequence (e.g., MSGLN-DIFEAQKIEWHE) into a fusion protein, which is subsequently acted upon by E. coli biotin ligase (BirA) in the presence of biotin and ATP to covalently attach biotin into such a genetically-engineered receptor fragment. A biotin-modified receptor fragment may then be attached to the template via streptavidin, which binds with high affinity to both biotin groups in the template and to the biotin group receptor fragment.

Complexes of this invention can, in certain embodiments, be considered as further comprising a membrane comprising a phospholipid component comprising a metal moiety selective for an amino acid residue of the fragment component. In certain embodiments, and as used to illustrate the broader aspects of this invention, a nickel nitrilotriacetic acid moiety can be used to modify a phospholipid such as but not limited to 1,2-dioleoyl-sn-glycero-3-phosphocholine. In such a manner, the phospholipid components of this invention can be used as templates for assembly of a plurality of the aforementioned receptor signaling complexes—either homogeneously by way of suitably dimensioned and prepared bilayer vesicles, or heterogeneously in conjunction with an appropriate solid support.

As provided below, data in support of this invention has been collected using small and large unilamellar vesicles as a template. As an extension of the unilamellar vesicle architecture, which is based in prior art, the present approach can be expected to function with other templates in suspension (a homogeneous format), or alternatively formed on solid substrates (a heterogeneous format). Homogeneous (e.g., suspendable) templates include, but are not limited to, other types of lipid assemblies, such as large multilamellar vesicles, self-assembled lipid nantoubes, supported membranes, and also polymeric materials. Generally, such vesicles or other template architectures can comprise any compound or composition providing amphiphilic properties, capable of bilayer membrane formation, modified as described herein or as would otherwise be known in the art for specific binding affinity with a suitably-modified receptor component. For example, without limitation, such a templating agent can comprise a suitably-modified polymer or co-polymer, comprised of poly(ethyleneglycol). Solid supports include, but are not limited to, supported lipid monolayer and bilayer membranes, and self-assembled monolayers (SAMs). Such supported lipid membranes may be prepared by known methods—which include deposition of monolayer and bilayer membranes on prepared substrates by Langmuir-Blodgett techniques, or through the fusion of vesicles to hydrophobic surfaces in the wells of immunoassay plates—synthetically modified as would be understood in the art for desired, selective interaction with a receptor fragment of this invention.

As such, the present invention can also include a method of using a homo- or heterogeneous template to assemble receptor signaling complexes and/or to restore the biochemical activity of a signaling pathway. Certain embodiments of such a method comprise 1) providing a phospholipid component in a medium suitable for vesicle formation, such a component comprising a cationic metal moiety (e.g., cationic) selective for chelation of an amino acid residue; 2) introducing a receptor fragment component to the medium, the fragment component comprising at least one amino acid with affinity for selective coupling bonding or chelating interaction with the phospholipid component; and 3) complexing the fragment component with a signaling protein introduced thereto. The phospholipid, receptor fragment and signaling protein components are as described above. Likewise, such a method can further include introduction of an adaptor protein to facilitate complexation, and/or methylation or other receptor modification conducive to enhanced pathway activity. With reference to certain embodiments, as demonstrated below, this invention provides a method of using histidine-nickel nitrilotriacetic acid affinity interaction to assemble cytoplasmic receptor fragments en route to signaling complexes of the sort described above.

As demonstrated herein, the present invention can further include a method to assay activation of a bacterial signaling transduction pathway. More specifically, in the context of the *E. coli* chemotaxis signaling pathway, such a method can comprise 1) providing a receptor signaling complex, as described herein and can be assembled on a phospholipid membrane of this invention; 2) introducing adenosine triphosphate and a phosphorylation protein to such a complex; and 3) determining phosphotransferase activity by monitoring the rate of triphosphate hydrolysis. The rate of hydrolysis indicates the degree of activation and subsequent signal transduction.

As will be evident to those skilled in the art made aware of this invention, the present complexes and related methods can be applied to any signal transduction pathway through straightforward modification of the components, fragments and/or use thereof. For example, while the analysis of signaling pathways can be approached through a determination ATPase activity, other measures of activity, such as the extent of protein phosphorylation, or the rate of GTP hydrolysis, may serve as indicators of activity provided that suitable affinity-tagged receptor fragments, the corresponding phospholipid components and detection reagents are used. The complexes, methods and/or assays of this invention are limited only by the availability of a cytoplasmic receptor fragment suitably modified for affinity interaction with a similarly available phospholipid selective for fragment chelation. While FIGS. 1-4 are presented in the context of the assembly and activity of a particular *E. coli* signaling pathway via measurements of ATP hydrolysis rate and extent of complex formation, the data, results and associated embodiments would be considered by those skilled in the art as demonstrating the broader aspects of this invention applicable to other biochemical or cellular systems, other assays of activity, other analyses involving receptor complexes and other means of biomimetic organization/activation thereof.

For instance, complexes, assemblies and/or related methods of this invention can comprise signaling components from other bacteria (without limitation, e.g., *Proteobacteria*) and other micro-organisms exhibiting chemotaxis systems analogous to those illustrated above, from such organisms that are homologous on the DNA level. As such, the complexes, assemblies and/or related methods of this invention can comprise one or more amino-tagged receptor components homologous to a methyl-accepting chemotaxis protein of which *E. coli* Tar, Tsr, Trg and Tap are representative, modified as, understood in the art for attachment to the templating membrane of the sort described herein. Similarly, the complexes, assemblies and/or methods of this invention can comprise homologs of an adaptor protein (e.g., CheW), a signaling protein (e.g., CheA) and/or a response regulator protein (e.g., a substrate of CheA, CheW).

Further, as would be understood by those skilled in the art, there are inherent organizational similarities between the bacterial chemotaxis signal transduction pathway and transmembrane signaling systems from cells in all three kingdoms (archaea, prokaryotes and eukaryotes). Accordingly, the complexes, receptors and/or methods of this invention can comprise proteinaceous components from a wide range of cellular transmembrane signaling pathways; that is, suitably-modified cytoplasmic domains of a type I and/or type II transmembrane proteins, or a mixture of cytoplasmic domains, useful as described herein to restore biochemical activity. Such components either possess enzymatic activity or have recognition motifs for recruitment of signaling and/or adaptor proteins. In particular, without limitation, such proteinaceous components can comprise proteins from the prokaryotic superfamily, members of which exhibit 2-component signaling pathways.

In accordance with this invention, template-directed assembly methods, components and reagents of the type described herein may be used to restore the function and activity of any signal transduction system in which complexes of signaling complexes, either transient or stable, are required for activity. As such, broader aspects of the present invention can be illustrated in the context of the *E. coli* chemotaxis-signaling pathway and uses an engineered cytoplasmic fragment of the aspartate receptor (Tar-CF), the adaptor protein CheW, the protein kinase enzyme CheA, and the kinase substrate, CheY and the receptor modifying enzyme CheR. These resulting data, which demonstrate the restoration of CheA activity by template-assembled Tar-CF and the ability of template-assembled Tr-CF to serve as a substrate of CheR, also demonstrate covalent modification to modulate the binding of CheW and CheA, and consequently the activity of CheA.

The underlying architectural analogy of this *E. coli* transmembrane signaling system to other systems—set into motion by ligand-receptor and/or cell-cell interactions—are numerous and evident in the literature (3-5). Examples include, but are not limited to (i) the JAK-STAT class of pathways, which, for example, mediate the proliferation and differentiation of blood cells, (ii) receptor tyrosine kinase (RTKs) pathways that are exemplified by the nerve, epidermal, fibroblast and transforming growth factor receptors, and (iii) The B-cell and T-cell receptor signaling pathways, in which immunoreceptor tyrosine activation motifs (ITAMs) located in the cytoplasmic portions of the B-cell and T-cell receptor complexes act to recruit adaptor and signaling proteins to the membrane surface. In each example and in numerous others in the art (3-5), receptors are instrumental in recruiting cytoplasmic signaling elements, adaptor proteins, enzymes and membrane-associated proteins, into arrangements that modulate pathway activity. Accordingly, the template-assembly methods described herein are applicable to the study of these and other such signaling pathways.

Figure 5:
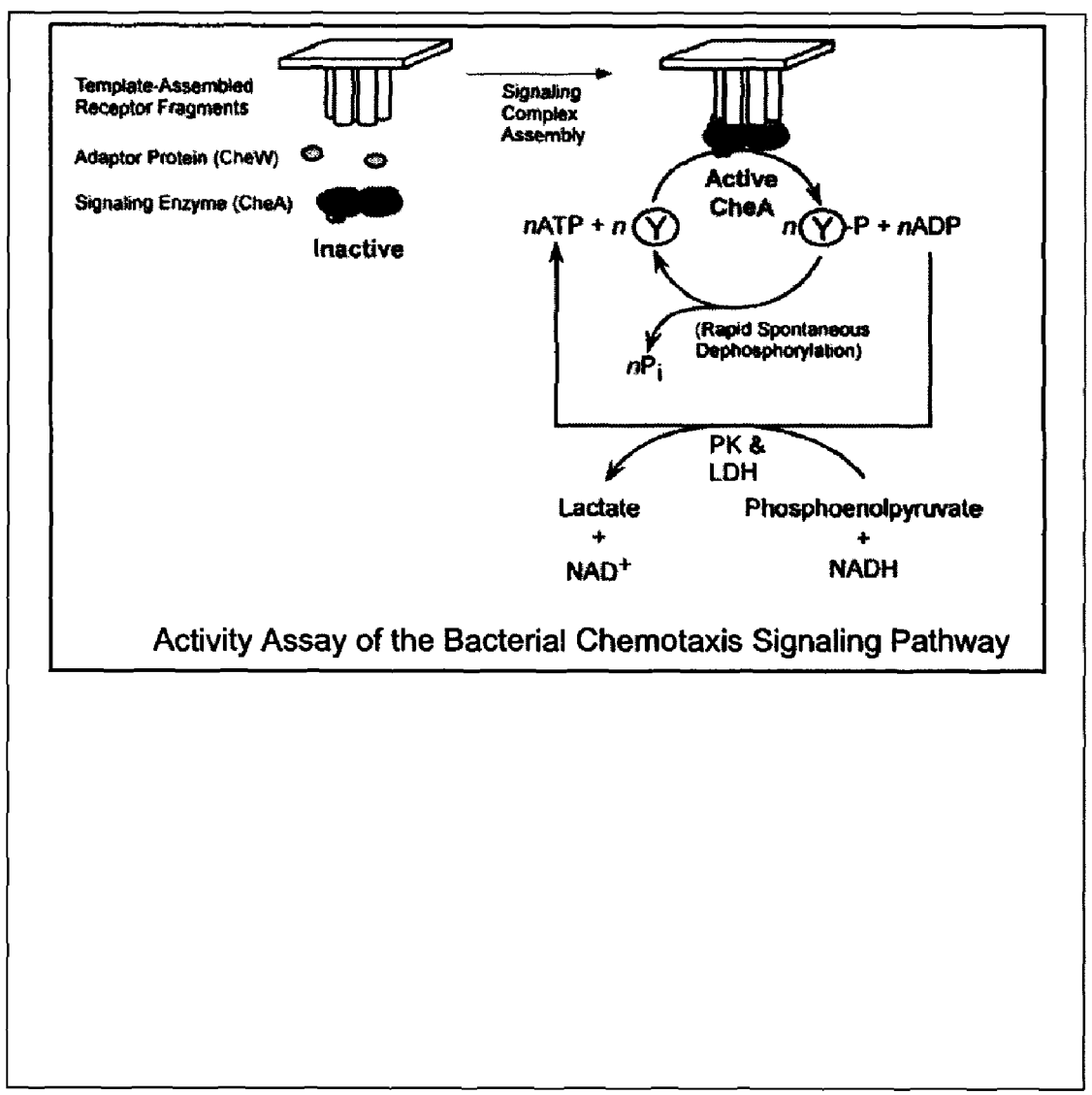
FIG. 5. With reference to example 2, a schematic illustration of an activity assay of an *E. coli* chemotaxis signaling pathway. Template-assembled receptor fragments (CF) are incubated with adaptor protein (CheW) and the autophosphorylating signaling enzyme (CheA) to generate active signaling complexes. In the presence of ATP and the phosphate accepting substrate CheY (Y) transfer of the gamma phosphate from ATP to CheA and from CheA to CheY takes place, creating ADP. ATP is reformed from ADP by the regenerating system that consists of the enzymes PK and LDH and the substrates phosphoenolpyruvate and NADH. The time rate of change in absorbance of NADH provides an indication of the rate of the ATP utilization by CheA.

FIG. 1 illustrates a scheme used to generate CF/CheW/CheA complexes with the vesicle-templating approach. For simplicity the CF is depicted in the coiled-coil hairpin dimer arrangement found in the x-ray structure (28) (FIG. 1A), although the extent of CF dimerization in solution and on the surface is not known. CF is randomly distributed in solution (FIG. 1B), but orients on binding to a vesicle outer surface via the Ni—NTA—histidine interaction, perhaps as depicted in FIG. 1C. The CF orientation in FIG. 1C is consistent with the observation of complete binding to vesicle (>95% of the CF co-sediments with vesicles), which reasonably excludes other orientations requiring a larger area per CF molecule bound (i.e. side-on versus end-on binding). See, Example 6. Ternary complexes of CF, CheW and CheA are then formed on the vesicle surface and the CheA phosphotransferase activity is measured in the presence of excess CheY in a coupled steady-state ATPase assay (FIG. 1D and FIG. 5).

Activation of CheA by Surface-Assembled CF. The histogram of CheA activity in FIG. 2A shows the effect of surface anchoring on CheA activity. CheA activity is significantly larger in the presence of Ni—NTA-SUVs compared to samples without vesicles, irrespective of the level of covalent modification on the CF. The trend of increasing activity (e.g., ATP molecules hydrolyzed per second per mole of CheA in the sample) with increasing levels of CF covalent modification, which is mimicked by replacing glutamates, E, with glutamines, Q, at the methylation sites (45), has been observed in previous studies of ternary (receptor-CheW-CheA) complexes formed with intact receptor molecules (8-12) and has been attributed to variations in the degree of CheA activation within the complex. These data provide evidence for a receptor-CheW-CheA complex of increasing stability as the level of modification is increased, and an activity that remains constant within the complex. The kinase activation experiments involving intact receptors generally have not assessed the fraction of CheA bound (8-12); in one instance where it was assessed qualitatively (9), the trend in complex stability as a function of covalent modification agrees with the current observations. A similar increase in stability as a function of the level of covalent modification (from EEEE to QQQQ) has also been observed with soluble supramolecular signaling complexes, which are formed using Tar CF fusion proteins (and CheA and CheW) that possess an n-terminal leucine zipper dimerization motif (35,46).

Variation in the stability of the signaling complexes is evident in the CheW-dependence of CheA activity (FIG. 2B) and vesicle binding (FIG. 2C) for signaling complexes made with CFs in different levels of covalent modification (EEEE, QEQE, QQQQ). The rise and fall in activity and binding are consistent with the known properties of CheW, which binds both to CheA and to the receptor cytoplasmic domain (6,47). Initially, CheW may facilitate an increase in the phosphotransferase and vesicle-binding activities through a CF-CheW-CheA bridging interaction. Increasing the CheW concentration further leads to saturation of the binding sites on CheA and CF, and consequently the CheA enzyme and vesicle-binding activities both lessen. The relative stabilities of CF/CheW/CheA complexes are apparent in the maximum values for activity and binding, and the CheW concentrations at which these maxima occur. The $CF_{QQQQ}$-containing complex is judged to be most stable since it has the largest maximum values of CheA activity and binding ($f_{Bound}$~0.95) at the smallest CheW concentration (<5 μM). The $CF_{EEEE}$-containing complex is the least stable, which is reflected in the smaller maximum values of activity and $f_{Bound}$ (~50% of $CF_{QQQQ}$ complexes), and the significantly larger CheW concentration at which the maximum is observed (~12 μM). A model for complex formation, which assumes that the CheA activity is proportional to $f_{Bound}$ captures the salient features of these data, and estimates the relative stability of complexes. The result of the analysis with this specific model (described in Examples 4 & 5), indicates that $K_{complex}$, an indicator of signaling complex stability, decreases over 100-fold as covalent modification on the CF decreases from the highest to the lowest level.

These results provide evidence that vesicle-templated CFs are functionally similar to intact receptors in the absence of (attractant) ligand, since the cytoplasmic domains activate CheA in both situations. Evidence of this functional similarity is based on a common structural organization from an analysis of a limited number of lock-off and timer-of-dimer (tod) mutations (21,48), which are located in the cytoplasmic domain at the positions shown in FIG. 1. Lock-off mutations mimic attractant-bound ternary complexes by producing complexes that are inactive in the absence of ligand (48,49). The lock-off allele, a serine-461 to leucine (S461L) mutation in the intact Tar protein, is located close to the sites of methylation. Tod mutations are known to disrupt the trimer-of-dimer interaction in the homologous Tsr protein (21), and are located near the turn in the coiled-coil hairpin. The two alleles tested correspond to the point mutations E383A and V382P in Tar.

CheA and CheW binding, and also CheA activation, were measured using vesicle-templated CFs. CheA activation (FIG. 3) was reduced significantly by all of these mutations, but CheA and CheW binding were retained to varying degrees, relative to wildtype CFs in the corresponding level of covalent modification (Table 1, below). The lock-off S461L CF (QEQE) retained substantial binding strength overall, which is consistent with the known ability of lock-off mutant receptors to compete for a limited pool of CheA and CheW in mixtures with activating receptors (49). The lower amounts of CheA and/or CheW binding exhibited by CFs containing tod mutations is consistent the disrupting effect that these types of mutations can have on the formation of receptor patches in vivo (21). The interference with kinase activation by the tod mutations is evidence that trimer-of-dimer-like interactions are also present in the vesicle-templated CFs, en route to CheA activation.

TABLE 1

Normalized CheA Activity, and CheA and CheW Bound Fractions to Vesicles Presenting Wildtype CFs[a]

| Modification Level | Phosphotransferase Activity s$^{-1}$ (per mol CheA bound) | Fold Activation[b] | f$_{Bound}$(CheA) | f$_{Bound}$(CheW) |
|---|---|---|---|---|
| EEEE | 15.7 ± 1.6 | 212 ± 22 | 0.59 ± 0.04 | 0.37 ± 0.03 |
| QEQE | 10.9 ± 0.4 | 147 ± 5 | 0.83 ± 0.01 | 0.64 ± 0.02 |
| QQQQ | 13.2 ± 0.3 | 178 ± 4 | 0.93 ± 0.01 | 0.87 ± 0.01 |

[a]Averages and uncertainties (standards errors of the mean) were calculated from triplicate samples. Sample compositions were 30 µM CF, 560 µM total lipid (1:1 DOPC:DOGS-NTA-Ni$^{2+}$) in the form of SUVs, 1.2 µM CheA, and either 5 µM (CF$_{QQQQ}$ and CF$_{QEQE}$) or 15 µM (CF$_{EEEE}$) CheW.
[b]The Fold Activations are the activities of the CF/CheW/CheA complexes divided by the activity of 5.0 µM CheA in solution (0.074 s$^{-1}$ per mol of CheA).

Surface-Assembly Enhances CF Methyl-Accepting Activity. The adaptation branch in the chemotaxis pathway involves reversible receptor methylation and demethylation, which are catalyzed by a methyltransferase and a methylesterase, respectively (25). Receptor methylation is a result of methyl group transfer from s-adenosyl-L-methionine (SAM) to specific glutamic acid residues in the cytoplasmic domain of MCPs (50-52). The process of methylation has been demonstrated to occur, at least in part, by a mechanism that involves transmethylation in which the transferase binds to the cytoplasmic domain through a tethering interaction and catalyzes methyl group transfer on a cytoplasmic domain of an adjacent receptor subunit through active site—substrate site interactions (17-19).

Figure 4:
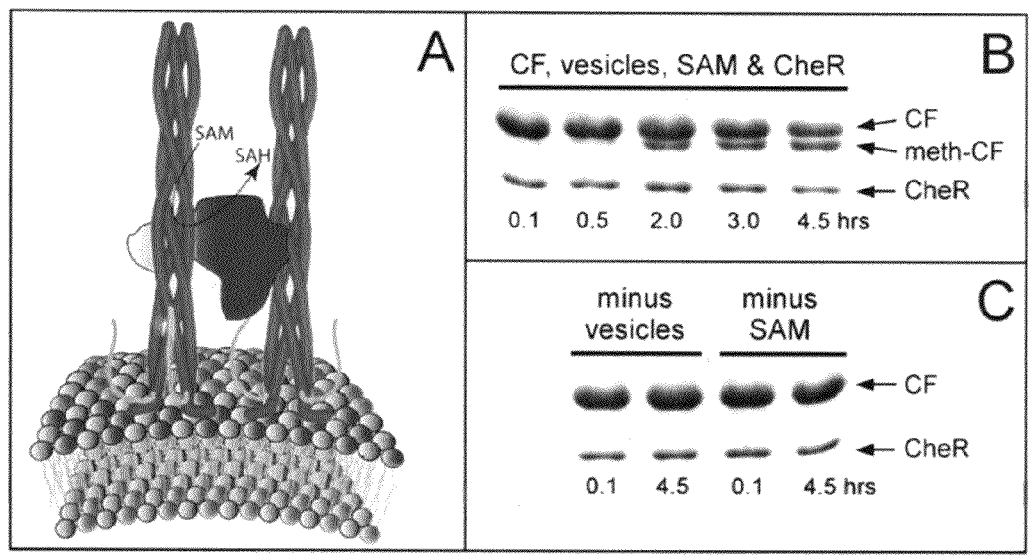
FIG. 4. CheR-Catalyzed Methylation of Vesicle-Templated CF. A: An illustration depicting methyl group transfer from s-adenosyl-L-methionine (SAM) to CF, promoted by transferase (CheR) binding to the CF c-terminus, to generate methylated CF (meth-CF) and s-adenosyl-L-homocysteine (SAH). B: The change in electrophoretic mobility of methylated CF indicates the reaction progress in a sample containing $CF_{EEEE}$, vesicles, SAM and CheR (~35% at 4.5 h). C: Minus vesicle and minus SAM controls.

Surface-assembled CF, in accordance with this invention, can generate the close associations between cytoplasmic domains for efficient methylation. FIG. 4A illustrates how the vesicle surface might facilitate CF transmethylation. The role of surface-assembly in promoting efficient CF methylation was assessed by comparing the extent of methylation of CF on vesicle surfaces relative to CF in solution. As the data in FIG. 4 demonstrate, substrate activity is enhanced significantly by binding to the vesicle surface. The SDS polyacrylamide gels in FIG. 4 show that only in the presence of vesicles, SAM and transferase does the CF convert to a more rapidly migrating band corresponding to methylated protein (FIG. 4B). The faster migrating band was not observed in the vesicle-minus and SAM-minus controls (FIG. 4C), suggesting that vesicle binding enhanced for substrate activity and that the more rapidly migrating band was not due to proteolysis of the CF, respectively. The use of vesicle-templating for efficient methyl group incorporation was also verified by scintillation counting using tritiated SAM as the methyl group donor (data not shown).

The polyhistidine tag has found previous widespread use as a convenient and effective genetically-encoded affinity tag for protein purification and screening applications, through the interaction of the histidine tag with metal-chelator complexes such as nickel-nitrilotriacetic acid (53-55). The histidine tag—Ni—NTA interaction has also been used in biosensor applications (54-57), and as a method for generating 2D protein crystals when the Ni—NTA moiety is present as a headgroup in lipid monolayers (37,58-60). However, use thereof in the present invention—to restore the functional properties of membrane-associated proteins—is neither disclosed nor taught in the art. The results described above demonstrate the significant effect that binding receptor fragments to vesicles surfaces can have in restoring biochemical activity. Complexes of transmembrane receptors, membrane-associated adaptor proteins, and cytoplasmic enzymes are a ubiquitous feature of signaling cascades (3-12). The architecture of these complexes and their rates of assembly and disassembly are a key to understanding the regulation of these biochemical processes. The vesicle-templating approach presented herein can be used in conjunction with such studies.

Application of this method to the bacterial chemotaxis system restores both the kinase activating and the methyl-accepting properties to the CF. Based on these observations, it is believed that binding to a template, e.g., in the form of either solid support or vesicle surface, promotes a lateral organization among CF subunits that resembles the organization of cytoplasmic domains in receptor-containing membranes. This conclusion is supported by the similar effects that lockoff and tod point mutations produce in templated CF and intact receptors, and suggests that inter-dimer interactions, e.g. a trimer-of-dimer organization (21,28), are involved in kinase activation. Also, the mutations appear to generate the kinase-inactive phenotype through different mechanisms, either by producing inactive complexes or by disrupting complex formation. The CF with the lockoff mutation retains significant CheA and CheW binding affinity while forming inactive signaling complexes; CFs with the tod mutations form inactive complexes at the expense of protein-protein interaction strength to varying degrees.

Experiments of the type set forth above also led to the observation that signaling complex stability can be influenced by receptor modification. This may prove to be a significant factor in regulating kinase activity in the cell since bacteria like E. coli integrate the effects of the different chemoeffector concentrations through a set of homologous receptors (13). CheA is the principal protein through which chemotactic responses are mediated. Therefore by regulating the extent of CheA association with (and activation by) receptors via covalent modification can provide a means to weigh the response to the various chemo-effectors, which can be present simultaneously at vastly different concentrations.

EXAMPLES OF THE INVENTION

The following, non-limiting examples and data illustrate various aspects and features relating to the receptor complexes and/or methods of the present invention, including the assembly of receptor signaling complexes on a biomimetic cell/support component, such complexes comprising a range of receptors modified as described herein for desired interaction with a particular cell/support component—as are available through the synthetic methodologies described herein. In comparison with the prior art, the present complexes and assembly methods provide results and data which are surprising, unexpected and contrary thereto. While the utility of this invention is illustrated through the use of several receptor fragments and signaling or adaptor proteins, it will be understood by those skilled in the art that comparable results are obtainable with various other receptor fragments or signaling proteins or combinations thereof, chemically or structurally modified as required for interaction with a biomimetic cell membrane/support component of this invention, depending upon a particular signal transduction pathway under consideration.

Protein Purification. The chemotaxis proteins CheA, CheR, CheW, CheY and Tar CF were purified according to established protocols (9,17,38). Tar CF was expressed from the plasmid pHTCF (17), which generates a protein that contains residues 257 to 553 of E. coli Tar, a vector-encoded hexahistidine affinity tag at the n-terminus (MRGSHHHHH-HGSPM$_{257}$ . . . ), and the wildtype pattern of amidation (QEQE) at the methylation sites (Gln295, Glu302, G 309, Glu491). pHTCF derivatives pSM100 and pSM101, which produce CF in the deamidated ($CF_{EEEE}$) and fully-amidated ($CF_{QQQQ}$) forms respectively, were constructed with standard site-directed mutagenesis methods and verified by sequencing. Signaling and receptor component protein concentrations were determined with the Lowry assay according to manufacturer's instructions ($D_c$ Protein Assay, Bio-Rad Laboratories). Purified and concentrated proteins were flash frozen in liquid nitrogen and stored at −75° C. Tsr, Tap and Trg CF's can be expressed with appropriate encoded affinity tags by analogous protocols, as would be understood by those skilled in the art.

Example 1

Assembly of Vesicle-Templated Signaling Complexes. SUVs were prepared from chloroform solutions of DOGS-NTA-Ni$^{2+}$ and DOPC (Avanti Polar Lipids) in a 1:1 molar ratio, which were evaporated under a nitrogen stream until a dried lipid film was obtained. Assay buffer (pH 7.5, 75 mM Tris-HCl, 100 mM KCl, 5 mM MgCl$_2$, 2 mM TCEP, 5% DMSO) was added to produce a 2 mg/mL lipid concentration, the film was hydrated for 20 min. at 25° C., and then the sample was bath sonicated at 30° C. (Branson Model 2510) until the solution clarified (~70 min.). To prepare large unilamellar vesicles (LUVs), hydrated lipid films were generated as described above, but the lipids were resuspended by gentle vortexing and the suspension was then extruded through filters with pores of defined sizes between 50 and 1000 nm. LUVs prepared in this manner are of various sizes, which are referred to either by the pore size through which extrusion took place or by the diameters of the LUVs that were measured by dynamic light scattering (DLS). SUVs prepared by sonication were found to have diameters of 30 nm by DLS. LUVs prepared by extrusion through filters with 50, 100 or 1000 nm pores had diameters of 90, 120 and ~500 nm, respectively. SUVs and LUVs were also made with DOGS-NTA-Ni$^{2+}$:DOPC molar ratios other than 1:1 for the purpose of controlling the 2-dimensional concentration of DOGS-NTA-Ni$^{2+}$ and thus the CF 2-dimensional concentration. For this purpose, the relative molar concentrations of DOGS-NTA-Ni$^{2+}$ and DOPC in the chloroform solutions prior to evaporation were adjusted to a desired ratio, typically between 1:20 and 3:2 DOGS-NTA-Ni$^{2+}$:DOPC.

Isothermal titration calorimetry was used to confirm the unilamellar nature of the SUV and LUV templates. Titration experiments led to an estimate of sixty percent DOGS-NTA-Ni$^{2+}$ in the outer leaflet of the SUV membrane and available for CF binding (data not shown). Titration experiments with LUVs provided evidence that fifty percent of the DOGS-NTA was accessible to Ni$^{2+}$ binding. These values were determined from the relative endpoints of titrations between nickel and SUVs containing DOGS-NTA using a matched pair of samples, one in buffer (outer leaflet accessible) and the other in buffer plus 1% octyl glucoside (all sites accessible).

Vesicle-bound signaling complexes were generated in a 75 μL sample volume by incubating vesicles (280 μM in DOGS-NTA-Ni$^{2+}$) and 30 μM CF in assay buffer for 2 min. at 25° C., followed by the addition of CheA (1.2 μM) and CheW (0-35 μM) with gentle vortexing and incubation at 25° C. for 3.5 hr.

Vesicle samples were analyzed for signal complex formation by separating the vesicle-bound protein using sedimentation (125,000×g for 15 min. in a Beckman TLX ultracentrifuge with a TLA120.2 rotor). Samples of free (supernatant) and total protein (an aliquot removed prior to sedimentation) were analyzed on SDS-polyacrylamide gels (15% weight/volume acrylamide, BioWhittaker Molecular Sciences) with software-assisted scanning densitometry (GS-700 Densitometer, Molecular Analyst, vers. 1.4, Bio-Rad Laboratories).

Example 2

Enzyme Assays. CheA-CheY phosphotransferase activity was measured in a steady-state coupled spectrophotometric ATPase assay (39,40) on 2 μL aliquots withdrawn from the samples (incubated for ~3.5 hr. at 25° C.). ATPase activity was measured immediately (30 s) after diluting the aliquots 100-fold into buffer with 50 μM CheY and assay reagents (2.5 mM PEP, 4.0 mM ATP, 250 μM β-NADH and 4 units of PK/LDH enzymes, obtained from Sigma-Aldrich). Specific phosphotransfer rates (s$^{-1}$) were determined from the absorbance change at 340 nm (d[ADP]/dt=−6220 dA$_{340}$/dt) relative to the activity of 5.0 μM CheA (0.074 s$^{-1}$), which was regarded as the solution activity of dimeric CheA. The activity of 50 μM CheY samples was subtracted as background. See, FIG. 5.

Example 3

The ability of CF to act as substrate for CheR was tested using 30 μM CF$_{EEEE}$ incubated with vesicles (1:1 DOPC:Ni—NTA-DOGS, 560 μM total lipid). Reactions were initiated by the addition of CheR and SAM at final concentrations of 6 μM and 10 mM, respectively. 20 μL aliquots were removed at 0.1, 0.5, 2, 3, and 4.5 hr, quenched in the course of preparing the samples for SDS-PAGE analysis, and resolved on 15% gels. The extent of the CF methylation reaction was estimated by the appearance of a protein band of increased mobility using densitometry, which is a known result of receptor methylation (8). See, FIG. 4.

Example 4

Curve Fitting. CheA activation and binding as a function of the CheW concentration were analyzed with a model based on pair-wise associations between CF (C), CheW (W) and CheA (AA) according to equilibrium expressions (Equations 1 to 4), mass conservation relationships (Equations 5 to 7), and expressions for the fraction of CheA bound to vesicles f$_B$, Equation 8) and CheA activity (Act, Equation 9):

  (1)

  (2)

  (3)

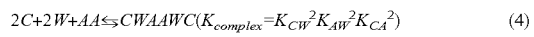  (4)

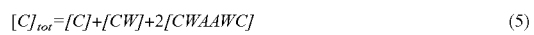  (5)

$$[W]_{tot}=[W]+[AAW]+2[WAAW]+2[CWAAWC] \quad (6)$$

$$[AA]_{tot}=[AA]+[AAW]+[WAAW]+[CWAAWC] \quad (7)$$

$$f_B=[CWAAWC]/([AA]+[WAA]+[WAAW]+[CWAAWC]) \quad (8)$$

$$Act=Act_0+f_B*Act_{Max} \quad (9)$$

$Act_0$ and $Act_{Max}$ are the background and maximum (100% CheA-bound) CheA activities, respectively. The constraints and assumptions of this model were chosen to be consistent with the experimental conditions and observations. (i) CheA was assumed to be present only as a dimer, since the total CheA concentration in the samples was about three-fold larger than the dissociation constant for CheA dimerization (38,39). (ii) Direct interactions between CF and CheA were neglected in the absence of CheW since CheA exhibited little binding to vesicles in the absence of CheW. (iii) The approximate proportionality between the activity and $f_B$ versus [W] data was interpreted to be consistent with a single surface-active species (CWAAWC).

Example 5

Estimates of $K_{complex}$. Nonlinear least-squares fits were conducted in Origin© (OriginLab Corporation, Northampton, Mass.) by an algorithm that generated estimates of $f_B$ and Act using Equations 1 to 9 of the model in Example 4, the total protein concentrations ($[C]_{tot}$, $[AA]_{tot}$, $[W]_{tot}$) defined by the experiment, and trial values of the adjustable parameters $K_{CW}$, $K_{AW}$, $K_{CA}$, and $Act_0$. The parameters were adjusted iteratively in the NLS fitting engine of Origin by the Levenberg-Marquardt method until the errors were minimized. In these fits, the values for $[AA]_{tot}$, $[W]_{tot}$ and $[C]_{tot}$ were shared among the three sets of data ($CF_{QQQQ}$, $CF_{QEQE}$ and $CF_{EEEE}$). $[AA]_{tot}$ was fixed to the molar concentration of CheA dimer used in the experiments (0.6 µM). $Act_{Max}$ was set to the average normalized activity (13.5 s$^{-1}$) observed with all three levels of CF modification (FIG. 2A and Table 1). $Act_0$ was permitted to adjust in the fits, as were the individual association constants. $[C]_{tot}$ was fixed at 10 µM, which corresponded approximately to the concentration of surface-bound CheW at saturation in a 30 µM solution of vesicle-bound CF (data not shown). A systematic analysis of the influence of $[C]_{tot}$ on fit results revealed that relative complex stabilities, e.g. $L_{complex}(QQQQ)/K_{complex}(EEEE)$, were insensitive to the assigned value of $[C]_{tot}$ over a range of 10-30 µM. The fit of the data in FIG. 2B by the model and the constraints described above resulted in values for $K_{complex}$ of 1.3, 0.09 and 0.002 µM$^{-4}$ for complexes formed with $CF_{QQQQ}$, $CF_{QEQE}$, $CF_{EEEE}$, respectively, and a value for $Act_0$ of 0.36±0.14 s$^{-1}$. Fits to the CheW-dependence of CheA binding ($f_{Bound}$, FIG. 2C) generated estimates for $K_{complex}$ of 4.6, 1.0 and 0.014 µM$^{-4}$ in $CF_{QQQQ}$, $CF_{QEQE}$ and $CF_{EEEE}$-containing complexes, respectively.

Example 6

Controlling the Surface Concentration of Templated Receptor Fragment to Regulate Activity. The average surface area available for templated receptor fragments can be estimated from the total surface area of the vesicles, the number of available binding sites on a vesicle and the total concentration of the receptor fragment that is to be templated. By way of an example, when a 1:1 molar ratio of DOPC and DOGS-NTA-Ni$^{2+}$ lipid is used to create the vesicle, the average area available for templating each CF is estimated to be ~770 Å$^2$. This estimate is achieved by (i) assuming a value of 70 Å$^2$ for the surface area per molecule of DOPC and DOGS-NTA-Ni$^{2+}$ (41), (ii) a determination of the percent accessible DOGS-NTA-Ni$^{2+}$ molecules out of the total number present in the sample by titration methods (this value is 60% for small unilamellar vesicles), and (iii) the sample composition 280 µM DOGS-NTA-Ni$^{2+}$, 280 µM DOPC, and 30 µM CF (receptor fragment). The average area of the template available to each CF molecule is the product between the number of accessible lipid molecules per CF, which is given by 0.6*(280+280)/30 (=11) and the area per lipid molecule (70 Å$^2$). This product gives the estimate cited above (770 Å$^2$). Under these conditions, the CF molecules are expected to be oriented 'end-on' on the template, which is illustrated in FIG. 1C and FIG. 1D. Based on known CF structure: the end on cross-section is estimated to be between ~330 and ~500 Å$^2$, or 2 to 3 times the cross-sectional area of an α-helix (~165 Å$^2$, ref. 42-44), and arises from the two α-helices in the CF coiled-coil hairpin configuration plus unstructured polypeptide at the carboxyl terminus. The area required for 'side-on' binding is estimated to be ~2500 Å$^2$ per CF molecule, in which a CF dimer occupies a rectangle defined by the approximate width (25 Å) and length (200 Å) of the dimer (28,30).

Figure 6:
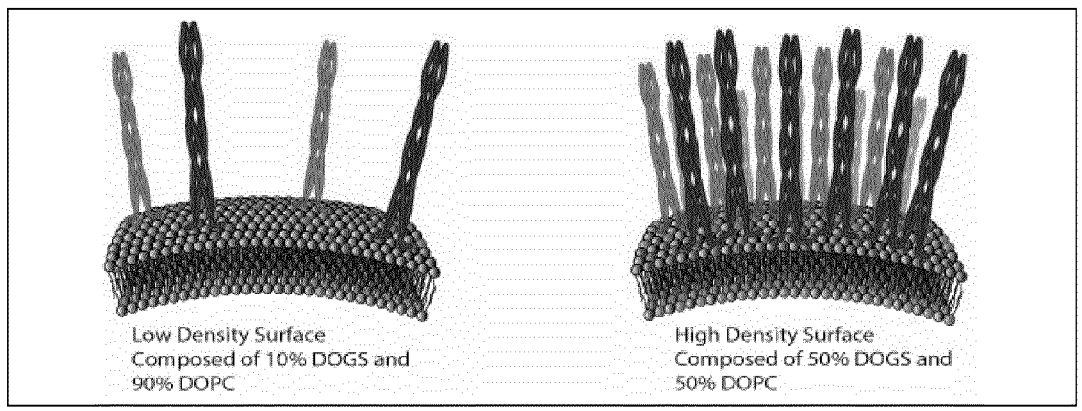
FIG. 6. A Diagram That Depicts Relative Low and High Densities of Templated CF. Lower 2-dimensional concentrations of CF on the template surface are generated by using lower percentages of DOGS-NTA-Ni$^{2+}$ in the binary mixture with DOPC. The templated CF on the left depicts the situation with a template made from 10% DOGS-NTA-Ni$^{2+}$ and 90% DOPC, which is expected to generate a 2-d CF concentration ~5 fold lower than the 2-d concentration shown on the right, which is formed by templating CF on vesicles formed with a 50:50 DOGS-NTA-Ni$^{2+}$:DOPC mixture.

The foregoing examples illustrate template-facilitated signaling enzyme activity measured under conditions characterized by a 1:1 DOPC to DOGS-NTA-Ni$^{2+}$ template composition, which generate a relatively large 2-dimensional concentration, or in other terms, a relatively small value for the template surface area per receptor fragment. Different formulations for the template can be made, wherein the fraction of DOGS-NTA-Ni$^{2+}$ in the DOGS-NTA-Ni$^{2+}$/DOPC mixture is varied, so that the average available template surface area changes accordingly. For example, a formulation with a 9:1 DOPC:DOGS-NTA-Ni$^{2+}$ molar ratio results in a 5-fold increase in average area per CF, from ~770 to 3800 Å$^2$ per CF molecule, estimated using a calculation similar to that described above. FIG. 6 provides a schematic representation for these low and high 2-dimensional concentrations of receptor fragments assembled on two different template formulations, 9:1 and 1:1 DOPC:DOGS-NTA-Ni$^{2+}$, (FIG. 6, left and right, respectively).

Figure 7:
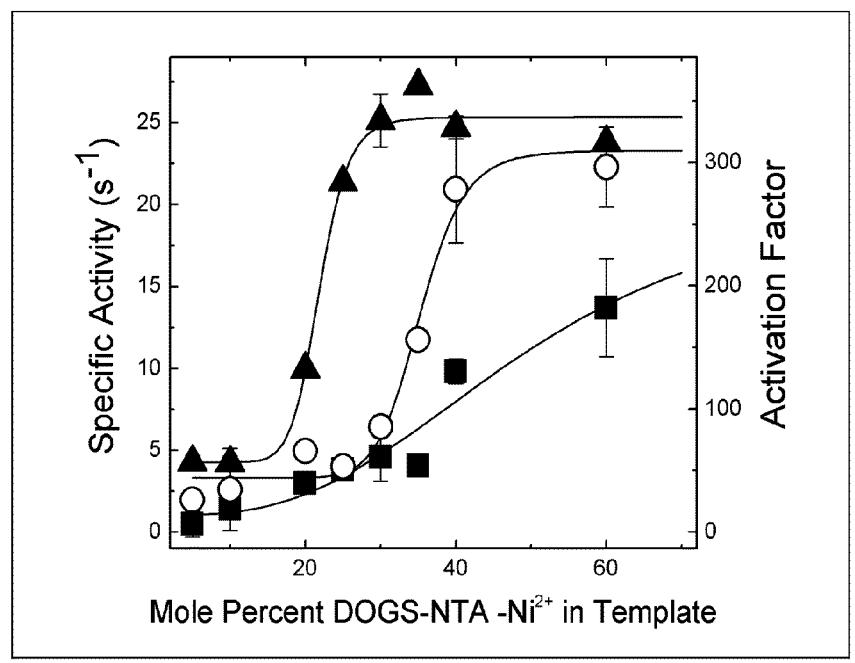
FIG. 7. CheA Activity in the Presence of Receptor Fragments Templated at Different Surface Areas and 2-D Concentrations. Left axis scale: ATP turnover per mole of CheA in the sample. Right axis scale: fold-activation on templates relative to the activity of CheA in solution. Legend: squares, SUVs; circles, LUVs (~90 nm) prepared by extrusion through 50 nm diameter pores; triangles, LUVs (~500 nm) prepared by extrusion through 1000 nm diameter pores. These samples were prepared with 280 μM DOPC, 280 μM DOGS-NTA-Ni$^{2+}$, 1.2 μM CheA, 10 μM CheW and 30 μM CF.

The results of experiments, which measure CheA enzyme activity as a function of the (2-dimensional) CF concentration are plotted in FIG. 7. FIG. 7 plots the ATP hydrolysis activity of CheA in the coupled assay using absolute units on the left hand axis (Specific Activity, s$^{-1}$) and on the right hand axis in units that are relative to the activity of CheA dimers in the absence of receptor fragments (Activation Factor). The 2-dimensional concentration, when expressed in units of template surface area per CF molecule, varied from a large area per molecule, ~7600 Å$^2$ (or equivalently, a small 2-dimensional concentration) that is set by the 5 mole percent DOGS-NTA-Ni$^{2+}$ composition of the template lipid mixture, to a relatively small area per molecule of about 650 Å$^2$ (or equivalently, a relatively large 2-dimensional concentration) that is set by the template composition of 60 mole percent DOGS-NTA-Ni$^{2+}$.

FIG. 7 demonstrates that CheA activities can depend significantly on the two-dimensional templated receptor fragment concentration. In these experiments the sample compositions were held constant with respect to the total concentrations of DOGS-NTA-Ni$^{2+}$ (280 µM), EEEE-CF (30 µM), CheW (5 µM) and CheA (1.2 µM). Thus, the observed differences in activity are attributed to the variations in the two-dimensional receptor concentration and the physical attributes of the template. Three different vesicle preparations were used: (i) SUVs, (ii) LUVs prepared by extrusion through a porous membrane with 50 nm pores, and (iii) LUVs prepared by extrusion through a 1000 nm porous membrane. In each case, CheA activities increased with the 2-dimensional receptor concentration, for SUVs (filled squares), 90 nm diameter LUVs (open circles), and ~500 nm diameter LUVs (filled triangles). The steep rise in CheA activity over a narrow range of 2-dimensional concentrations, i.e. 20 to 30% with the ~500 nm diameter LUVs and 30 to 40% with the 90 nm diameter LUVs), is indicative of the involvement of a cluster or configuration of fragment receptors in CheA activation.

A distinguishing feature of these three templates is the unperturbed vesicle diameter, which is the vesicle diameter in the absence of CF, CheW and CheA. SUVs have the smallest diameter in diameter (30 nm), LUVs prepared by extrusion through 1000 nm pores have the largest (nominally 500 nm). FIG. 8D depicts the relative template diameters of an SUV (left) and the progressively larger LUVs (right). Also, a cluster of CFs is depicted on the 500 nm LUV surface (only part of which is shown). Because particle diameter is the only salient difference among these templates, the differences in CheA activity as a function of the 2-dimensional receptor fragment concentration (which is evident in FIG. 7), is attributed to differences in template surface curvature and/or curvature strain. To summarize, the signaling activity is shown to depend on (i) the 2-dimensional receptor concentration and (ii) a controlled template attribute, e.g., the unperturbed vesicle diameter.

Example 7

Figure 8:
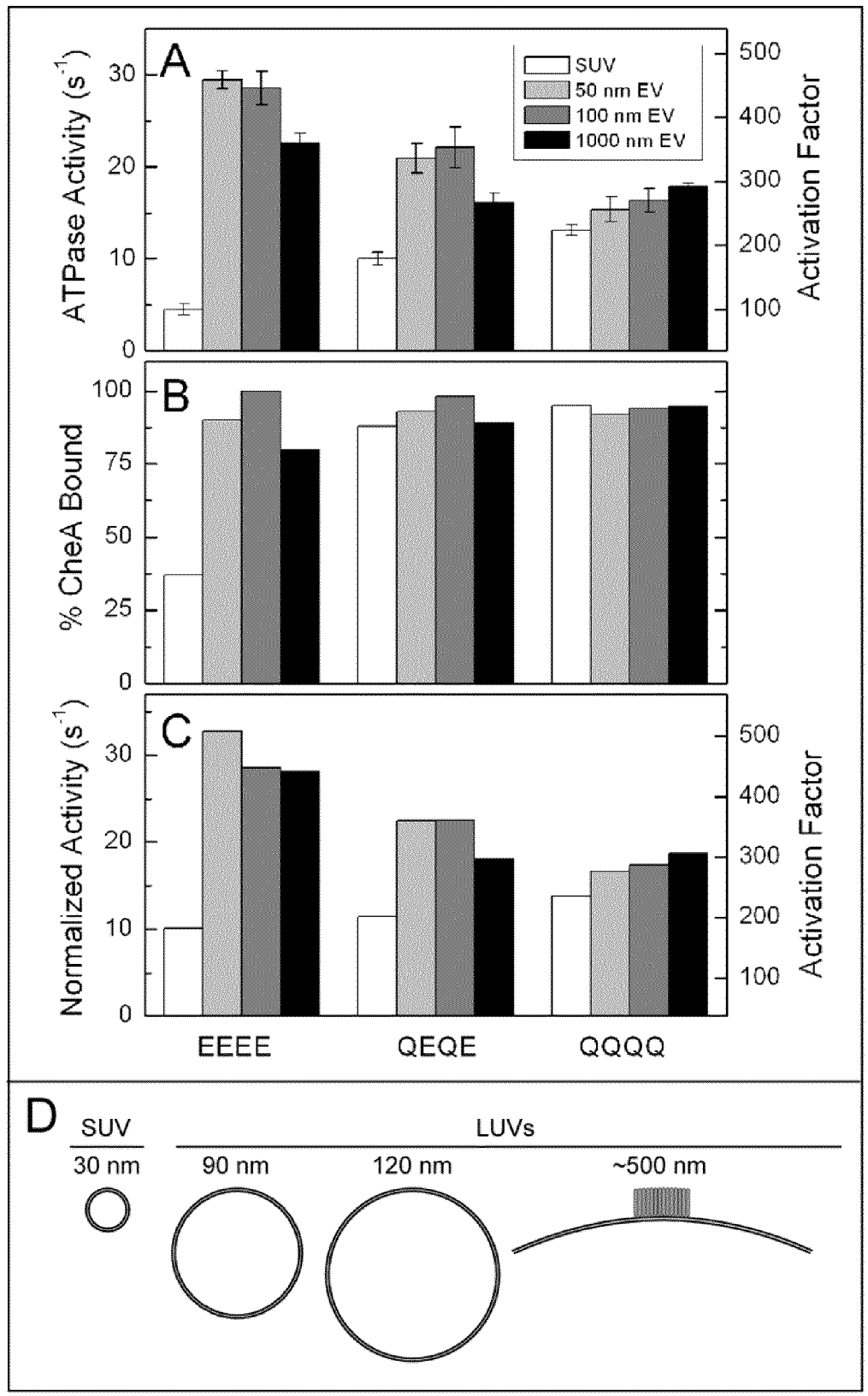
FIG. 8. CheA Activity and Binding on Vesicle Templates Prepared by Different Methods. CFs were templated onto either SUVs (white columns) or LUVs prepared by extrusion through porous membranes of different pore size (50 nm, light gray columns; 100 nm, dark gray columns; 1000 nm, black columns). Also, CFs in the different covalent modification states were tested: EEEE (left group), QEQE (middle group), QQQQ (right group). For each situation, the activity (s$^{-1}$) per mole of CheA present (panel A), the percent CheA bound to CF (and CheW) on vesicle templates (panel B), and the activity (s$^{-1}$) per mol of CheA bound to templated CF (panel C), was determined. These samples contain 280 μM DOPC, 280 μM DOGS-NTA-Ni$^{2+}$, 1.2 μM CheA, 5 μM CheW and 30 μM CF. Panel D: A schematic diagram to represent the relative diameters of SUVs and LUVs that were measured by dynamic light scattering. Only a portion of the ~500 nm diameter LUV is shown. For illustration purposes, a scaled CF cluster, oriented 'end-on', is depicted on this surface.

The Use of Unilamellar Vesicles of Varying Diameter. Further characterization of the relationships among template size, the net charge on the receptor fragment and the formation of active signaling complexes is provided in FIG. 8. The histograms in FIGS. 8A, 8B and 8C show CheA specific activity ($s^{-1}$), the extent of signaling complex assembly (the percent template-bound CheA), and the normalized CheA activity (which assumes only template-bound CheA is active), respectively. These data were collected using 1:1 DOPC:DOGS-NTA-$Ni^{2+}$ templates. In each panel (A, B & C), the three groups (of four columns) are data of CFs in the different states of covalent modification, that correspond to different chemical forms of the receptor fragments, in which four specific amino acid residues in the CF are either all glutamate residues (EEEE, left), two glutamine and two glutamate residues (QEQE, middle), or four glutamine residues (QQQQ, right). The negative charge on the CF decreases as these residues are changed from glutamates to glutamines, and this has demonstrated physiological significance. In each group of four, the columns represent different unperturbed template diameters, and present data obtained with SUVs (white bars), 90, 120 and ~500 nm EVs (light gray bars to black bars, left to right). Template-facilitated formation of signaling complexes is promoted on vesicles of all diameters. In the best situation, nearly 500-fold activation of CheA (the activity of CheA in the presence of template, relative to the activity without template) is observed. As discussed above (and also shown in FIG. 2A), the extent of signal complex formation was observed to increase as the covalent modification was varied from EEEE to QQQQ when the templates were SUVs. This feature is observed reproducibly (white bars in FIGS. 8A & B), and is a distinguishing feature of the SUV template, because the extent of CF/CheW/CheA complex formation on LUV templates is, in contrast, uniformly high (FIG. 8B, light gray to black columns) at all levels of covalent modification under the same experimental conditions (280 μM DOPC, 280 μM DOGS-NTA-$Ni^{2+}$, 30 μM CF, 5 μM CheW and 1.2 μM CheA).

It is also evident that the CheA activity is generally larger with the LUV templates than the SUV templates (FIGS. 8A & B). In these experiments the CF protein is applied to the template in such a way to generate the same surface concentrations; thus is it probable that the difference in activity and binding are related to vesicle surface curvature (illustrated in FIG. 8D). That the SUV template behaves differently from the LUV templates of any diameter may be attributed to curvature strain of the vesicle, which is near the maximum possible value with the SUV template. The high curvature and resistance to deformation may work against the formation of active signaling complexes. This is overcome through the use of the LUV templates. When these results are considered with the preceding examples, it is thus evident that the use of a template is the key element, and that the nature of template can varied in a controlled fashion to further improve, and/or tailor, the performance of the signaling system.

Example 8

Emergent Phenomena Illustrated Through the Use of Signaling Mutations. Point mutations were also introduced (receptor fragments differing by one amino acid residue) into the CFs to assess effect on assembly and signaling activity in the template system. The dominance of such mutations in vivo (refs. 21 and 48), which are known to influence interactions between receptor subunits, correlates with the extent to which activity can be rescued in vitro, in the binary mixtures with wild-type CF. Also, the effect of these mutations on CheA and CheW binding is consistent with this activity-rescue correlation; superdominant and/or epistatic mutations tend to assemble signaling complexes as or more effectively than wild-type CF through stronger CheW binding interactions, while the mutations that exhibit recessive and rescuable phenotypes assemble signaling complexes less effectively, which is due to weaker CheW binding interactions. Experiments have been conducted with a mixture of two histidine-tagged CFs (wildtype CF and a signaling mutant) assembled on a vesicle surface. The results demonstrate that the binding and activation of signaling proteins can be influenced by such mutations in a manner that is not immediately obvious from a study of the mutant form of the CF alone. These results also provide proof for the feasibility of using such mixtures and the requirement of their use to discern non-obvious properties of the signaling pathway.

Figure 9:
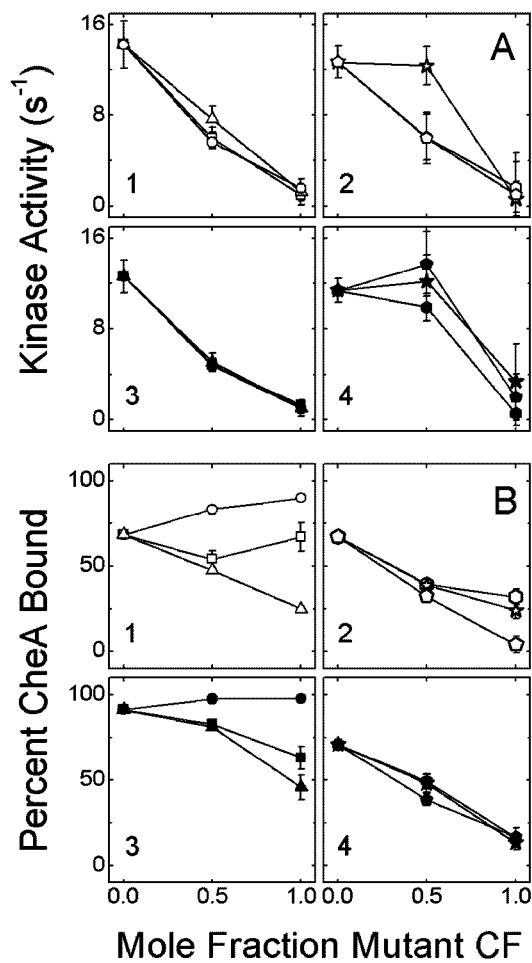
FIG. 9. CheA Activity and Binding with Binary Mixtures of Templated CF. CheA activity (A) and the percent CheA bound to templated CF (B) in the presence of CheW. The activity and binding of CheA were screened in 1:1 wildtype-CF:mutant-CF (0.5 mole fraction) mixtures and to provide comparisons, the wildtype and mutant-form CFs were templated in their pure forms (mutant CF mole fractions of 0.0 and 1.0, respectively). Open and filled symbols are data with unmodified (EEEE) and fully-modified (QQQQ) CFs, respectively. Samples contained a 250 μM DOPC—300 μM DOGS-NTA-Ni$^{2+}$ mixture suspended as SUVs, 1.2 μM CheA, 30 μM total CF, and either 4 μM or 15 μM CheW (in the QQQQ-CF and EEEE-CF containing samples, respectively). Symbol key: L376A: □,■; S325L: ○,●; S461L: △,▲; V382P: ◇,◆; E383A: ☆,★ I375P: ◯,●.
Figure 10:
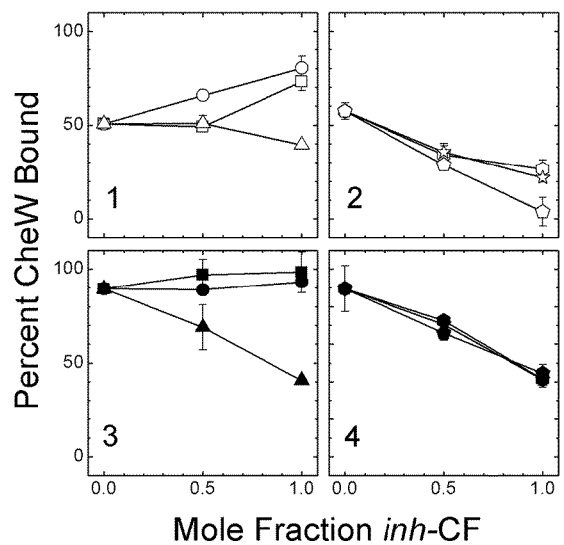
FIG. 10. CheW Binding to Binary Mixtures of Templated CF in the Presence of CheA. The CheW binding to 1:1 wildtype:mutant mixtures (0.5 mole fraction mutant CF) of templated CF was measured. To provide comparisons, CheW binding was also measured to the wildtype and mutant CFs templated in their pure forms (0.0 and 1.0 mutant CF mole fractions, respectively). Samples contained a 250 μM DOPC—300 μM DOGS-NTA-Ni$^{2+}$ mixture suspended as SUVs, 1.2 pM CheA, 30 μM total CF, and either 4 μM or 15 μM CheW (in the QQQQ-CF and EEEE-CF containing samples, respectively). Symbols are the same as defined in the legend to FIG. 9.

These data, which are plotted in FIGS. 9 through 12, are divided into two categories: (i) a survey of CheA activity and ternary complex formation (FIGS. 9 and 10), and (ii) in-depth analyses of selected binary mixtures. FIG. 9 plots the CheA kinase activity (FIG. 9A, top four panels) and the extent of ternary complex formation assessed by the fraction of CheA bound to vesicles (FIG. 9B, bottom four panels). CFs in the two extremes of covalent modification (EEEE, open symbols; QQQQ, closed symbols) were assessed for CheA-activating and signaling-complex-forming abilities, in template-assembled systems with 100% wildtype CF, 50% wildtype CF-50% mutant CF, and 100% mutant CF. The six point mutations that were screened for these properties were known, from previous studies, to either strongly disrupt cellular signaling function (S325L, L376A, S461L) or to have comparatively mild affects on function (V382P, E383A, I375P). (With reference to this terminology, consider S461L. S and L represent the single letter abbreviations for serine and leucine, respectively. S461L refers to a mutant form of the *E.* coli aspartate receptor in which the serine residue that is normally found at position 461 has been replaced with leucine. The other single letter amino acid abbreviations, A, E, I, V and P are for alanine, glutamate, isoleucine, valine and proline, respectively.) The strong and weak disruptors of signaling are separated in FIGS. 9 (and 10) to the left and right-hand panels, respectively.

Novel information, achieved from the analysis of these experiments, can be summarized as follows: (i) Strong disruptors always exhibit decreased activity in the 50:50 mixtures, weak disruptors can exhibit wildtype-like activity (FIG. 9A, compare panel 1 with 2 and panel 3 with 4). (ii) Signal complex formation, which is indicated by the degree of CheA and CheW binding, proceeds to a smaller extent when the weakly-disrupting mutations are present in the CF (relative to the wildtype CF). In contrast, the presence of strongly disrupting mutations can lead to similar or event greater levels of signal complex formation relative to the wildtype CF, but these complexes are inactive. This is evident in the steady decreases in CheA activity as the percentage of mutant CF increases in the binary mixtures (FIG. 9A, panels 1 and 3), but in these same samples, the level of CheA and CheW binding (shown in the corresponding panels of FIGS. 9B and 10, respectively) can remain at high levels. In summary, the use of binary mixtures of different receptor species, as illustrated here with the wildtype and mutant chemotaxis receptor fragments, leads to new insights into function, which would not be found from the study of signaling complexes composed exclusively of either the wildtype or mutant forms alone. Also, templating binary, ternary or even multicomponent mixtures of receptors can be easily implemented in conjunction with this invention, which provides a unique approach for recreating the complex interactions that are generally expected to occur in membrane-based signaling processes.

Example 9

Figure 11:
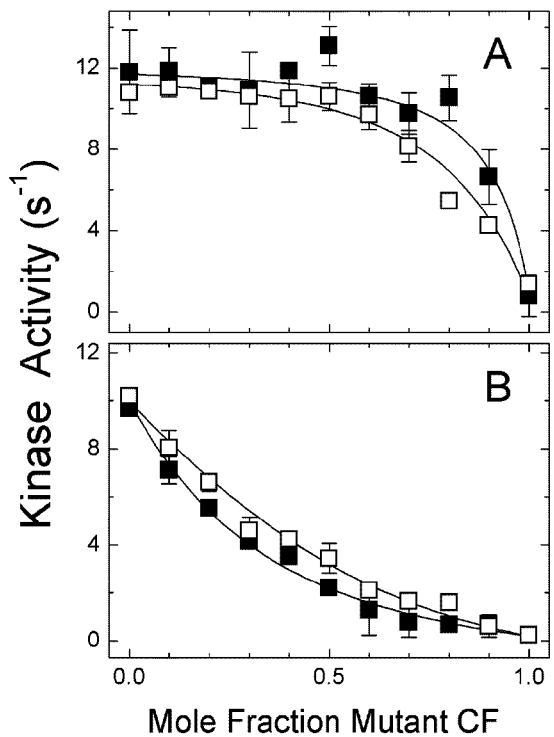
FIG. 11. Competitive Effects in Templated Binary Mixtures of Mutant and Wildtype Forms of CF. CheA activities are plotted as function of the mole fraction in wildtype and mutant (E383A) QQQQ-CF mixtures (A), and in wildtype and mutant (S325L) QQQQ-CF mixtures (B), with 4 either μM (■) or 15 μM CheW (□) present, and the SUV and protein compositions specified in FIG. 10. The curves through the data were determined by nonlinear least squares fits to a competitive binding model.
Figure 12:
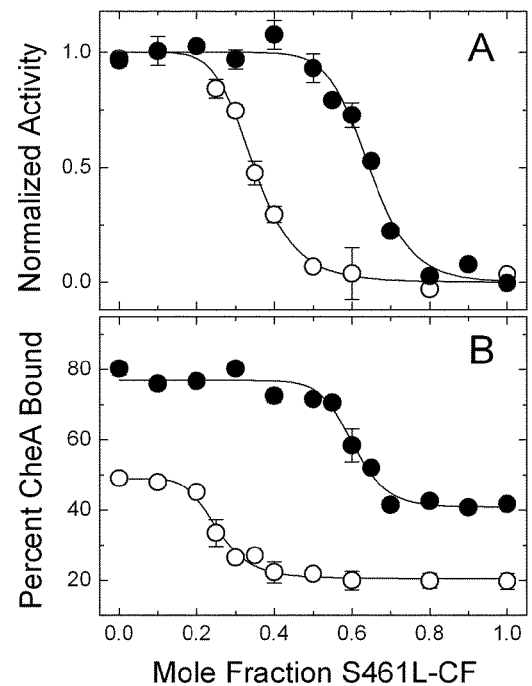
FIG. 12. Cooperativity in the Activity and Binding of CheA with Templated Binary Mixtures of Wildtype-CF (wt-CF) and Mutant-CF S461L (S461L-CF). Kinase activities (A) are presented as fractions of the maximum value observed. The extent of complex formation is represented as the percent CheA bound out of the total CheA present (B). wt-$CF_{QQQQ}$/S461L-$CF_{QQQQ}$ (●), wt-$CF_{EEEE}$/S461L-$CF_{EEEE}$ (○).

Competitive and Cooperative Interactions in Templated CF Mixtures. The utility of this invention is illustrated further in detailed analyses of CheA activity as a function of the binary mixture composition. FIGS. 11 and 12 shows the results of experiments with three signaling mutants (S325L, E383A, S461L). The CheA activity of wildtype-CF/E383A-CF binary mixtures, which is plotted in FIG. 11A, tolerates the interfering effects of the E383A mutant CF even at relatively large mole fractions. This property is consistent with a competitive interaction between the wildtype and the E383A CFs for CheW and CheA. Wildtype CF binds CheW more strongly (data not shown) and also competes more effectively for CheA, which results in the persistence of significant activity at the large mole fractions of this mutant. In contrast, CheA decreases more rapidly on the templated wildtype-CF/S325L-CF mixtures (FIG. 11B), which is consistent with the observed stronger CheW binding of the S325L-CF relative to wildtype (data not shown). As a result a greater proportion of the available CheW and CheA is expected to bind to S325L-CF, which leads to the formation of inactive signaling complexes. The curves drawn through these data sets (in both FIGS. 11A and 11B) are based on a mathematical model that incorporates the essential features of a competitive CheW and CheA binding interaction, and correctly accounts for the relative CheW binding strengths and the dependence of the curves on CheW concentration. This analysis also serves to explain the effects produced in vivo, where these mutations are located in the intact receptor. Taken together, these results and the comparisons among them serve to validate the utility of the template assembly approach for providing detailed information about the signaling pathway that could not be achieved by an analysis of the pair-wise interactions between molecules.

In addition to the competitive effects just discussed, binary mixtures of templated CF exhibit cooperative regulation of CheA activity and ternary complex formation. The results of CheA activity and binding experiments conducted with wildtype-CF/S461L-CF mixtures, which are present in FIG. 12, provide evidence of cooperative interactions among the receptor fragments, which is manifested in the sigmoidal dependence of CheA activity and complex formation on CF composition (FIGS. 12A and 12B, respectively). These experiments were conducted on templated CF mixtures in which both the wildtype and S461L CFs were also either in the EEEE or the QQQQ modification state (open and filled circles, respectively). To quantify the degree of cooperativity, these data were fit to the Hill equation, from which the Hill coefficients ($n_H$) were found to be 5 and 12 for the EEEE-CF and QQQQ-CF mixtures, respectively. The covalent modification also proved to be influential in setting the inhibition midpoint, about 30 and 60 mole percent S461L-CF, respectively. As in the case with the analyses conducted with binary mixtures described above (wildtype and either E383A or S325L CFs), properties of the system emerge from template-directed assembly method that could not be recovered from a pair-wise interaction analysis of signaling proteins, which represents the prior art for analyzing the interactions and activity of signaling pathways. These data thus serve as evidence that efficient reconstitution of the signaling pathway reactions is facilitated by the template-directed assembly methodology in a manner that effectively reflects the relevant physiological properties of the system.

By extension of the data in these examples, signaling complexes/systems may be provided for function through two or more co-receptor proteins of different amino acid sequence and composition. More specifically, it is evident that mixtures of two or more histidine-tagged receptor fragments, corresponding to the aforementioned co-receptors or other localized proteins, can be assembled on a vesicle surface or a solid support in proportions as determined to bind and activate cellular signaling proteins (e.g., analogs of the aforementioned CheA and CheW proteins).

While the principles of this invention have been described in connection with specific embodiments, it should be understood clearly that these descriptions are added only by way of example and are not intended to limit, in any way, the scope of this invention. For example, data herein has been collected with templates of sonicated (or small) unilamellar vesicles (SUVs) and also larger unilamellar vesicles prepared by extrusion (LUVs), which are adaptable to high-throughput modes of analysis. The spectrophotometric measurement of ATPase activity described herein can, for example, be feasibly adapted for use in industry-standard automated plate readers, which can perform absorbance readings on a large number of samples in parallel (96 to ~1500). It is apparent from those practiced in the art of high-throughput screening methods that template-assembled signaling complexes can be generated by semi-automatically and/or robotically dispensing the reagents, that include the templates, signaling components, and detection reagents, in a sequential fashion. Such an approach will also permit a synchronized initiation of the activity assay, and thus facilitate high-throughput analyses of the conditions that activate and regulate the signaling pathway in the template-assemble signaling system, including, but not limited to, screens for the effects of potential therapeutic agents.

We claim:

1. An in vitro assembly for use in protein assays, said assembly comprising: a plurality of a first membrane-associated receptor protein domain component; and a lipid bilayer membrane comprising a first phospholipid component modified for binding with said first membrane-associated receptor protein domain component, said first membrane-associated receptor protein domain component having a binding affinity for said modified binding component and being coupled with said lipid bilayer membrane by interaction with said modified binding component to promote a two dimensional cooperatively interactive organization of said plurality of first membrane-associated receptor protein domain component that mimics a natural organization of said first membrane-associated modified phospholipid receptor protein component on a cell membrane; wherein said first-membrane-associated receptor protein domain component, when coupled with said lipid bilayer membrane, exhibits biological function that more closely mimics its function than the first membrane-associated receptor protein domain component in solution in the absence of the lipid bilayer membrane.

2. The assembly of claim 1 wherein said modified binding component comprises a metal moiety.

3. The assembly of claim 2 wherein said modified binding component comprises a nickel nitrilotriacetic acid moiety.

4. The assembly of claim 3 wherein said first membrane-associated receptor protein component comprises at least one histidine residue.

5. The assembly of claim 1 wherein said modified binding component comprises a maleimide moiety.

6. The assembly of claim 5 wherein said first membrane-associated receptor protein domain component comprises a cysteine residue.

7. The assembly of claim 1 wherein said membrane further comprises a second phospholipid component that does not have a binding affinity for said first membrane-associated receptor protein domain component; and wherein said modified binding component and second phospholipid component are present in relative amounts sufficient to at least partially affect the concentration of said first membrane-associated receptor domain protein domain component on said membrane.

8. The assembly of claim 7 wherein said modified binding component comprises DOGS-NTA-$Ni^{+2}$, and said second lipid component comprises DOPC, said modified binding component and second phospholipid component present in a ratio from about 3:2 to about 1:20.

9. The assembly of claim 1 wherein said membrane is a unilamellar vesicle.

10. The assembly of claim 9 wherein said vesicle has a diameter dimension up to about 1,000 nm.

11. The assembly of claim 1 wherein said first membrane-associated receptor protein domain component is selected from the cytoplasmic domains of methyl-accepting chemotaxis proteins.

12. The assembly of claim 11 wherein said assembly further comprises an adaptor protein complexed with said first membrane-associated receptor protein domain component.

13. The assembly of claim 1 wherein said first membrane-associated receptor protein domain component comprises a signal protein or a component of a signal protein.

14. The assembly of claim 13 wherein said signal protein is a phosphotransferase.

15. The assembly of claim 1 wherein said first membrane-associated receptor protein domain component is a transmembrane receptor component.

16. The assembly of claim 15 wherein said first membrane-associated receptor protein domain component is a first cytoplasmic domain of a transmembrane receptor.

17. The assembly of claim 1 wherein said assembly further comprises a plurality of a second membrane-associated protein component coupled to the membrane.

18. The assembly of claim 17 wherein said first membrane-associated receptor protein domain component is a first transmembrane receptor component and said second membrane-associated protein component is a second transmembrane receptor component.

19. The assembly of claim 18 wherein said first membrane-associated receptor protein domain component is a first cytoplasmic domain of a transmembrane receptor.

20. The assembly of claim 19 wherein said second membrane-associated protein component is a second cytoplasmic domain of a transmembrane receptor.

21. The assembly of claim 1 wherein said first membrane-associated receptor protein domain component comprises a cytoplasmic domain of at least one bacterial transmembrane receptor.

22. The assembly of claim 1 wherein said first membrane-associated receptor protein domain component is a component of a receptor selected from aspartate, serine, dipeptide, ribose/galactose and aerotaxis receptors.

23. The assembly of claim 22 wherein said first membrane-associated receptor protein domain component is an aspartate receptor comprising at least one histidine residue.

24. The assembly of claim 23 wherein said first membrane-associated receptor protein domain component is a cytoplasmic domain of the aspartate receptor comprising at least one histidine residue.

25. The assembly of claim 1 wherein said first membrane-associated receptor protein domain component is a kinase.

* * * * *